(12) United States Patent
Guo et al.

(10) Patent No.: US 11,814,677 B2
(45) Date of Patent: *Nov. 14, 2023

(54) METHODS AND SYSTEMS FOR SENSITIVE AND MULTIPLEXED ANALYSIS OF BIOLOGICAL SAMPLES USING CLEAVABLE FLUORESCENT STREPTAVIDIN AND ANTI-HAPTEN ANTIBODIES

(71) Applicant: ARIZONA BOARD OF REGENTS ON BEHALF OF ARIZONA STATE UNIVERSITY, Scottsdale, AZ (US)

(72) Inventors: Jia Guo, Tempe, AZ (US); Joshua LaBaer, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 228 days.

This patent is subject to a terminal disclaimer.

(21) Appl. No.: 17/138,287

(22) Filed: Dec. 30, 2020

(65) Prior Publication Data
US 2021/0198735 A1 Jul. 1, 2021

Related U.S. Application Data

(60) Provisional application No. 62/954,719, filed on Dec. 30, 2019.

(51) Int. Cl.
| | | |
|---|---|---|
| C12Q 1/68 | (2018.01) | |
| C12Q 1/6874 | (2018.01) | |
| C12Q 1/6876 | (2018.01) | |

(52) U.S. Cl.
CPC ......... *C12Q 1/6874* (2013.01); *C12Q 1/6876* (2013.01); *C12Q 2563/131* (2013.01)

(58) Field of Classification Search
CPC ................ C12Q 1/6874; C12Q 1/6876; C12Q 2563/131
See application file for complete search history.

(56) References Cited

U.S. PATENT DOCUMENTS

| | | | |
|---|---|---|---|
| 6,066,459 A | 5/2000 | Garini et al. | |
| 7,414,116 B2 | 8/2008 | Milton et al. | |
| 2008/0268462 A1* | 10/2008 | Kosmeder ............ | C07D 215/52 435/7.1 |

(Continued)

OTHER PUBLICATIONS

Bayani et al., Multi-Color FISH Techniques, Current Protocols in Cell Biology, 2004, 24(1):22.5.1-22.5.25.

(Continued)

*Primary Examiner* — Jezia Riley
(74) *Attorney, Agent, or Firm* — Quarles & Brady, LLP

(57) ABSTRACT

Provided herein are methods and systems for sensitive and multiplexed in situ analysis of samples such as biological samples using cleavable hapten linked targeting agents and cleavable detectably-labeled hapten-binding agents. In particular, provided herein are methods for multiplexed single-cell in situ biomolecule profiling in samples, including fixed or fresh tissues, and also allows the investigation of the different cell compositions and their spatial organizations in intact tissues through consecutive cycles of probe hybridization, fluorescence imaging, and signal removal.

20 Claims, 16 Drawing Sheets
(13 of 16 Drawing Sheet(s) Filed in Color)

(56) References Cited

U.S. PATENT DOCUMENTS

2015/0038355 A1* 2/2015 Tan ................ G01N 33/54393
   506/18
2022/0026433 A1* 1/2022 Guo ...................... G01N 21/64

OTHER PUBLICATIONS

Danilova et al., Integrated Cytogenetic Map of Mitotic Metaphase Chromosome 9 of Maize: Resolution, Sensitivity, and Banding Paint Development, Chromosoma, 2008, 117(4):345-356.

Fransz et al., Interphase Chromosomes in *Arabidopsis* are Organized as Well Defined Chromocenters from which Euchromatin Loops Emanate, PNAS, 2002, 99(22):14584-14589.

Leriche et al., Cleavable Linkers in Chemical Biology, Bioorganic & Medicinal Chemistry, 2012, 20(2):571-582.

Liao et al., Highly Sensitive and Multiplexed In-Situ Protein Profiling with Cleavable Fluorescent Streptavidin, Cells, 2020, 9:852, pp. 1-14.

Mondal et al., Highly Multiplexed Single-Cell In Situ Protein Analysis with Cleavable Fluorescent Antibodies, Angewandte Chemie International Edition, 2017, 56(10):2636-2639.

Roberts et al., Novel Method for the Production of Multiple Colour Chromosome Paints for Use in Karyotyping by Fluorescence In Situ Hybridisation, Genes, Chromosomes and Cancer, 1999, 25(3):241-250.

Sambrook et al., Molecular Cloning, A Laboratory Manual, Chapter 10, Working with Synthetic Oligonucleotide Probes, Cold Spring Harbor Laboratory Press, 2001, pp. 10.1-10.52.

Schrock et al., Multicolor Spectral Karyotyping of Human Chromosomes, Science, 1996, 273(5274):494-497.

Thermofisher Scientific, Selected Haptenylation Reagents and Their Anti-Hapten Antibodies—Table 4.2, The Molecular Probes Handbook, 2019, https://www.thermofisher.com/us/en/home/references/molecular-probes-t . . . elected-haptenylation-reagents-and-their-anti-hapten-antibodies.html, 2 pages.

Tijssen, Hybridization with Nucleic Acid Probes, Part I: Theory and Nucleic Acid Preparation, Chapter 2, Overview of Principles of Hybridization and the Strategy of Nucleic Acid Probe Assays, 1993, Elsevier, pp. 19-78.

* cited by examiner

FIGS. 9A-9F, CONTINUED
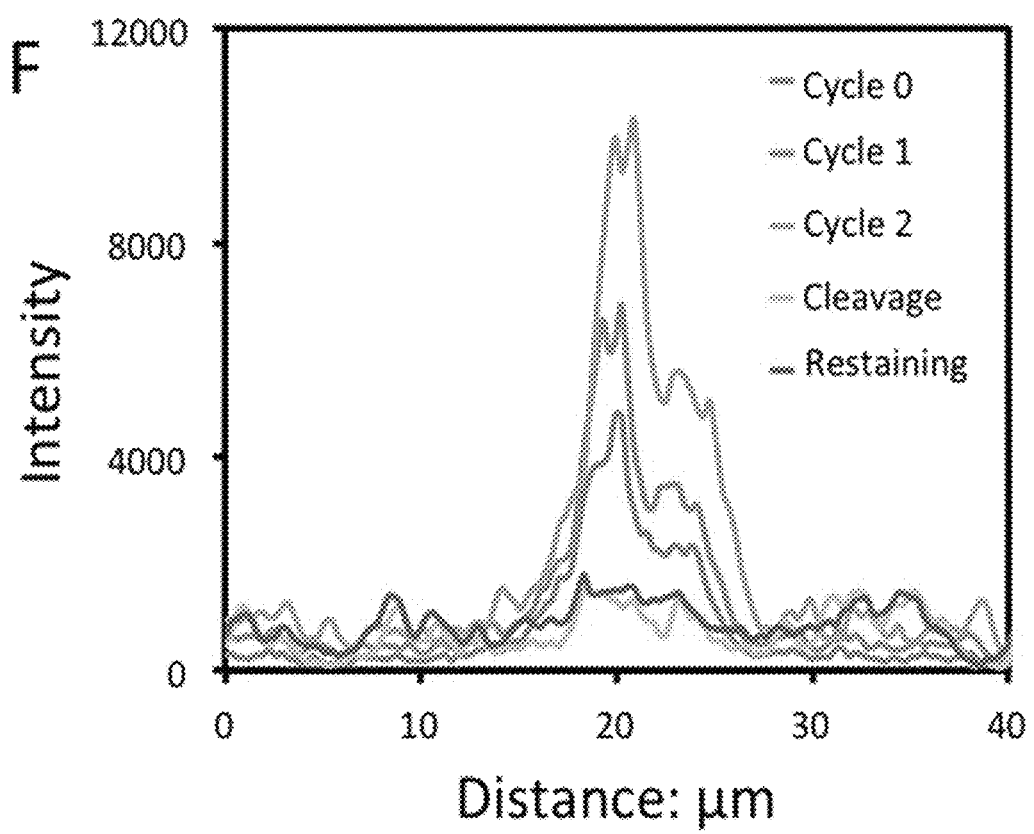

METHODS AND SYSTEMS FOR SENSITIVE AND MULTIPLEXED ANALYSIS OF BIOLOGICAL SAMPLES USING CLEAVABLE FLUORESCENT STREPTAVIDIN AND ANTI-HAPTEN ANTIBODIES

CROSS-REFERENCE TO RELATED APPLICATIONS

This application claims priority to U.S. Provisional Application No. 62/954,719, filed Dec. 30, 2019, which is incorporated by reference in its entirety for all purposes.

STATEMENT REGARDING FEDERALLY SPONSORED RESEARCH

This invention was made with government support under R01 GM127633 and R21 AI132840 awarded by the National Institutes of Health. The government has certain rights in the invention.

BACKGROUND

The ability to perform highly sensitive and multiplexed in situ protein and nucleic acids analysis is crucial to advance our understanding of normal physiology and disease pathogenesis. Comprehensive molecular profiling in single cells in situ holds great promise to reveal cell-to-cell variations and cell-microenvironment interactions, which are masked by population-based measurements. Various methods have been developed for multiplexed single-cell analysis. For example, immunofluorescence (IF) and fluorescence in situ hybridization (FISH) are well-established single-cell in situ molecular analysis platforms. However, only a couple of proteins or nucleic acids can be profiled in a single specimen using these methods, due to spectral overlap of commonly available organic fluorophores. To enable multiplexed in situ molecular profiling, a number of methods have been developed recently. In these methods, the detection tags are directly conjugated to the affinity probes, like antibodies and oligonucleotides. the existing methods have limited detection sensitivity, which impede the analysis of low expression proteins and short RNA. Additionally, due to the low sensitivity of the current methods, long imaging exposure time is required, which results in limited sample throughput and long assay time. Accordingly, there remains a need in the art for highly sensitive and multiplexed in situ methods of molecular analysis that permit characterization of a large number of biomolecules expressed with a wide range of expression levels in single cells in situ.

SUMMARY

In a first aspect, provided herein is a method of multiplexed in situ analysis of biomolecules in a tissue. The method can comprise or consist essentially of the following steps: (a) performing a first contacting step that comprises contacting a sample comprising biomolecules with a first hapten-conjugated targeting agent, the first hapten-conjugated targeting agent comprising a first targeting agent conjugated to the hapten via a cleavable linker, wherein the targeting agents are configured to specifically bind or hybridize to a target biomolecule in the contacted sample, and wherein the first contacting step occurs under conditions that promote binding or hybridization of the targeting agents to the target biomolecule; (b) performing a second contacting step that comprises contacting the sample with a hapten-binding composition comprising a hapten-binding agent linked to a detectable label via a cleavable linker, wherein the second contacting step occurs under conditions that promote conjugation/binding of the hapten-binding composition to the hapten of the first hapten-conjugated targeting agent; (c) imaging the sample after the second contacting step whereby a detectable signal generated from an interaction of hapten-conjugated targeting agents with the detectably-labeled hapten-binding composition is detected; (d) cleaving the cleavable linkers to remove the detectable label from the detectably-labeled happen-binding composition and unbound hapten; (e) blocking remaining hapten-binding agent with free hapten; and (f) optionally consecutively repeating the first and second contacting, imaging, cleaving, and blocking steps, each time with a new plurality of hapten-conjugated targeting agents for each subsequent cycle, wherein each utilized plurality differs from each other utilized plurality due to being configured to specifically bind or hybridize to a different target biomolecule. The plurality of biomolecules can comprise proteins, RNA, or DNA, or a combination thereof. The hapten-conjugated targeting agents can be biotin-conjugated antibodies or biotin-conjugated oligonucleotides, or a combination thereof.

The cleavable linker can be chemically cleavable, enzymatically cleavable, nucleophilically cleavable, electrophilically cleavable, photocleavable, metal cleavable, cleavable under reductive conditions, cleavable under oxidative conditions, cleavable using an acidic reagent, or cleavable using a basic reagent.

The cleavable detectably-labeled hapten-binding composition can be streptavidin and can comprise a fluorophore. The fluorophore can be selected from the group consisting of Cy5, TAMRA, ALEXA FLUOR™ 594, ATTO 647N, ATTO 700, ALEXA FLUOR™ 350, ALEXA FLUOR™ 532, ALEXA FLUO® 546, ALEXA FLUOR™ 568, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800, Texas Red, Cy2, Cy3.5, Cy5.5, and Cy7. The cleavable detectably-labeled hapten-binding composition can be streptavidin-N3-Cy5. Removing the detectable label can comprise chemically cleaving the detectable moiety. The method can further comprise washing to remove unhybridized targeting agents and non-specifically hybridized targeting agents following each second contacting step. The plurality of targeting agents can comprise biotin-conjugated synthetic DNA oligonucleotide probes, biotin-conjugated antibodies, biotin-conjugated peptide nucleic acids (PNAs), biotin-conjugated chemically modified oligonucleotides, or biotin-conjugated locked nucleic acids, or a combination thereof. The plurality of targeting agents can comprise hapten-conjugated polyclonal antibodies, hapten-conjugated monoclonal antibodies, or hapten-conjugated antigen-binding fragments thereof, wherein the hapten is selected from those listed in Table 1.

In another aspect, provided herein is a kit for detecting target biomolecules in a cell sample. The kit can comprise or consist essentially of a cleavable detectably-labeled hapten-binding agent and a written insert component comprising instructions for performing multiplexed in situ analysis of target biomolecules according to the methods of this disclosure. The cleavable detectably-labeled hapten-binding composition can be streptavidin-N3-Cy5. The kit can further comprise a plurality of hapten-conjugated targeting agents configured to bind or hybridize to a target biomolecule, where the hapten can be selected from those listed in Table 1. The plurality of hapten-conjugated targeting agents can comprise biotin-conjugated synthetic DNA oligonucleotide probes, biotin-conjugated antibodies, biotin-conjugated peptide nucleic acids (PNAs), biotin-conjugated chemically modified oligonucleotides, or biotin-conjugated locked nucleic acids, or a combination thereof. The plurality of hapten-conjugated targeting agents can comprise hapten-conjugated polyclonal or monoclonal antibodies, or antigen-binding fragments thereof. The kit can further comprise tris(2-carboxyethyl)phosphine (TCEP) and the written instruction component further comprises instructions for removing the detectable label from the detectably-labeled hapten-binding composition using the TCEP.

In a still further aspect, provided herein is a method for in situ analysis of biomolecules in a sample, the method comprising the following steps: (a) performing a first contacting step comprising contacting a sample comprising a plurality of biomolecules with a first hapten-conjugated targeting agent, the first hapten-conjugated targeting agent comprising a first targeting agent conjugated to the hapten via a cleavable linker, wherein the first targeting agent is configured to specifically bind or hybridize to a first target biomolecule in the sample, and wherein the first contacting step occurs under conditions that promote binding or hybridization of the first targeting agent to the first target biomolecule in the sample; (b) performing a second contacting step comprising contacting the sample of step (a) with a hapten-binding composition comprising hapten-binding agent linked to a detectable label via a cleavable linker, wherein the second contacting step occurs under conditions that promote conjugation of the hapten-binding composition to the hapten of the first hapten-conjugated targeting agent; (c) performing a third contacting step comprising contacting the sample of step (b) with a second orthogonal hapten labeled antibody for signal amplification, wherein the third contacting step occurs under conditions that promote binding of the second orthogonal hapten labeled antibody to the hapten-binding composition; (d) performing a fourth contacting step comprising contacting the sample of step (c) with a second hapten-binding composition comprising a second hapten-binding agent linked to a detectable label via a cleavable linker under conditions that promote binding of the second hapten-binding agent to the second orthogonal hapten labeled antibody; and (e) imaging the sample after step (d), whereby a detectable signal generated from an interaction of hapten-conjugated targeting agents with the hapten-binding agent is detected.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or patent application file contains at least one drawing in color. Copies of this patent or patent application publication with color drawings will be provided by the Office upon request and payment of the necessary fee.

The present disclosure will be better understood and features, aspects, and advantages other than those set forth above will become apparent when consideration is given to the following detailed description thereof. Such detailed description makes reference to the following drawings, wherein.

DETAILED DESCRIPTION

Figure 1:
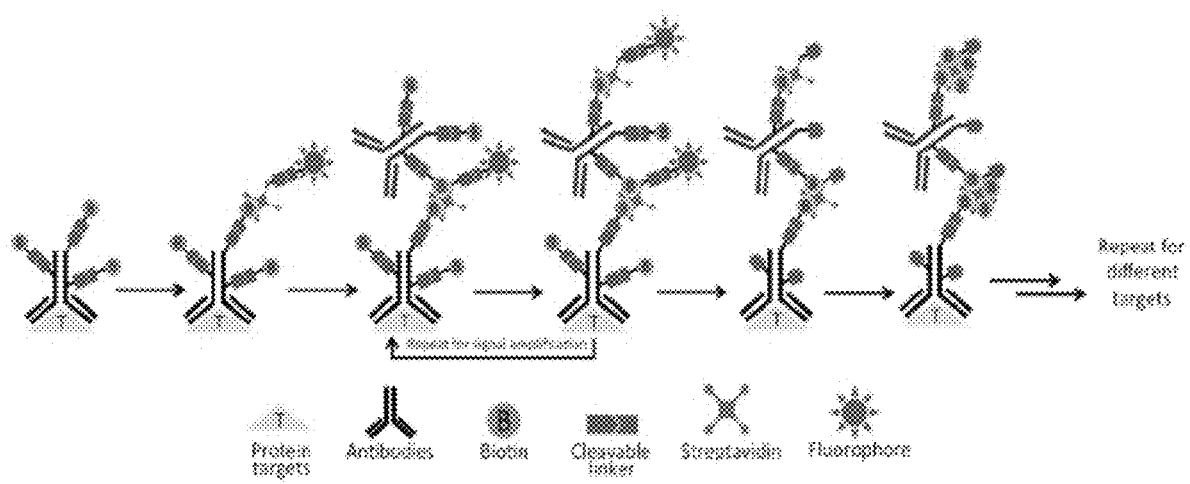
FIG. 1 illustrates highly sensitive and multiplexed in situ protein profiling with cleavable fluorescent streptavidin (CFS). In each cycle, the protein of interest is first targeted by cleavable biotin-labeled primary antibody, and then stained with CFS. Through layer-by-layer signal amplification using cleavable biotin conjugated antibodies and CFS, highly sensitive protein detection is achieved. After imaging, the fluorophores and the biotins unbound to streptavidin are chemically cleaved and subsequently streptavidin is blocked by biotin. Through reiterative cycles of target staining, signal amplification, fluorescence imaging, chemical cleavage and streptavidin blocking, comprehensive protein profiling can be achieved.

All publications, including but not limited to patents and patent applications, cited in this specification are herein incorporated by reference as though set forth in their entirety in the present application.

The methods and compositions provided herein are based at least in part on the inventors' study of highly sensitive and multiplexed in situ methods for molecular profiling of proteins and nucleic acids in single cells. Unlike conventional methods, which provide population-based measurements, the methods provided herein enable measurement of cell-to-cell variations of proteins and nucleic acids. The methods of this disclosure also enable analysis of cell-microenvironment interactions as well as detection of low-expression proteins and short nucleic acids. The presently described methods have increased sensitivity compared to conventional methods such as immunofluorescence or fluorescence in situ hybridization. In conventional methods, detection tags are directly conjugated to affinity probes, like antibodies and oligonucleotides. Without signal amplification, the existing methods have limited detection sensitivity, which impedes the analysis of low expression proteins and short RNA. Additionally, due to the low sensitivity of the current methods, long imaging exposure times are required, which result in limited sample throughput and long assay time. By contrast, the methods of this disclosure permit layer-by-layer signal amplification. As a result, the detection sensitivity and sample throughput can be increased by at least one order of magnitude. As the detection sensitivity increases by at least one order of magnitude, it allows the detection of low-expression proteins and short nucleic acids in biological samples, which are undetectable by other methods. Due to the high sensitivity of the presently described methods, imaging and assay times are also dramatically reduced. In addition, the assay does not damage the sample so multiple different targets can be assessed using a single sample. The sample may be any biological sample comprising proteins, nucleic acids (DNA or RNA) or carbohydrates. In some embodiments, the samples include a cell, a tissue, a paraffin embedded tissue section, a fresh tissue section, a frozen tissue section, a fixed tissue, fixed cells, or frozen cells. The ability to use a wide array of samples is an additional strength of the method. Suitably the sample is attached or adherent to a solid support.

Accordingly, in a first aspect, provided herein is a highly sensitive and multiplexed in situ method for detecting biomolecules such as proteins and nucleic acids in a biological sample. Generally, the method comprises contacting cleavable biotin or other hapten conjugated antibodies or oligonucleotides to a biological sample under conditions that promote binding to proteins or nucleic acids in the sample, followed by staining with cleavable fluorescent streptavidin or another hapten-binding agent (CFS). In another step, the contacted sample is incubated with a cleavable biotin-labeled orthogonal antibody followed by CFS. The contacted sample is imaged to generate quantitative single-cell protein expression profiles. In a next step, fluorophores and unbound biotins are removed by chemical cleavage. Any remaining streptavidin is blocked with biotin. The above-described steps can be repeated one or more times to analyze additional proteins or nucleic acids in the same sample.

Referring to FIG. 1, the method comprises five steps in each analysis cycle. First, for analysis of a protein in a sample, the sample is contacted with an antibody specific to the protein of interest, where the antibody is conjugated to a distinct cleavable hapten. For analysis of nucleic acids in a sample, the sample is contacted with an oligonucleotide probe configured to hybridize to the nucleic acid target, where the oligonucleotide probe is conjugated to a distinct cleavable hapten. The sample is also contacted with a detectably-labeled, cleavable streptavidin (e.g., CFS) or other agent capable of binding the hapten. In a second step, the contacted sample is incubated with a cleavable hapten-labeled orthogonal antibody followed by CFS. In a third step, fluorescence images are captured to generate quantitative single-cell expression profiles. In a fourth step, fluorophores and biotins unbound to streptavidin are removed by chemical cleavage and the remaining streptavidin is blocked with biotin in a fifth step. These steps allow for initiation of the next analysis cycle. Steps 1-5 can be repeated as desired. Through reiterative cycles of target staining, fluorescence imaging, fluorophore cleavage, and streptavidin blockage, a large number of different target biomolecules with a wide range of expression levels can be quantified in single cells of intact tissues in situ.

In some embodiments, the method of multiplexed in situ analysis of biomolecules in a sample comprising the following steps: (a) performing a first contacting step that comprises contacting a sample with a plurality of targeting agents conjugated to biotin via a cleavable linker, wherein the targeting agents are configured to specifically bind or hybridize to a target biomolecule in the contacted sample, and wherein the first contacting step occurs under conditions that promote binding or hybridization of the targeting agents to the target biomolecule; (b) performing a second contacting step that comprises contacting the sample comprising a plurality of biomolecules to streptavidin comprising a detectable label via a cleavable linker, wherein the second contacting step occurs under conditions that promote conjugation of the detectably-labeled streptavidin to biotin of the targeting agents; (c) imaging the cell after the second contacting step whereby a detectable signal generated from an interaction of biotin-conjugated targeting agents with the detectably-labeled streptavidin is detected; (d) removing the detectable label from the detectably-labeled streptavidin and unbound biotin; (e) blocking the remaining streptavidin; and (f) repeating the first contacting step, second contacting step, and imaging step with a different plurality of biotin-conjugated targeting agents, wherein each utilized plurality differs from each other utilized plurality due to being configured to specifically bind or hybridize to a different target biomolecule, whereby multiple target biomolecules are detected in situ in the same sample.

In some embodiments, an endogenous biotin removal step is performed prior to carrying out the steps described herein. For example, an endogenous biotin removal step is performed prior to the first contacting step.

In some embodiments, the method comprises an additional step wherein the tissue or biological sample is contacted with a second orthogonal labeled antibody for signal amplification.

In each analysis cycle, varied protein targets are first recognized by primary antibodies labeled with distinct cleavable haptens, such as biotin, fluorescein, TAMRA, and digoxigenin (DIG). Subsequently, streptavidin, anti-fluorescein, anti-TAMRA, and anti-DIG antibodies labeled with different fluorophores are applied to stain the protein targets and amplify the signals. In this way, multiple proteins are quantified simultaneously in each cycle. In some cases, haptens and their anti-hapten antibodies suitable for use according to the methods of this disclosure are selected from those set forth in Table 1. While use of the hapten pair of streptavidin and biotin is described herein and illustrated in the Examples, it should be understood that other haptens and their binding partners can be used in place of streptavidin and biotin. For example, a cleavable detectably-labeled digoxigenin (DIG) can be used in place of cleavable detectably-labeled streptavidin. In such cases, targeting agents (e.g., polyclonal or monoclonal antibodies) conjugated with anti-DIG antibody are used in the second contacting step.

TABLE 1

Selected haptenylation reagents and their anti-hapten antibodies

| Preferred Reactive Hapten(s) | Unlabeled and Labeled Anti-Hapten Antibodies (Hapten-binding agents) |
|---|---|
| Alexa Fluor 405, SE | Anti-Alexa Fluor 405/Cascade Blue dye |
| Alexa Fluor 488, SE | Anti-Alexa Fluor 488 dye |
| Alexa Fluor 488, SE | |
| Alexa Fluor 488, 5-TFP | |
| Alexa Fluor 488, 5-SDP | |
| 3-Amino-3-deoxydigoxigenin hemisuccinamide, SE | Anti-digoxigenin |
| Biotin-X, SE | Anti-biotin |
| Biotin-XX, SE | |
| Biotin-X, SSE | |
| Biotin-XX, SSE | |
| BODIPY FL-X, SE | Anti-BODIPY FL dye |
| BODIPY FL, STP ester | |
| Cascade Blue acetyl azide | Anti-Alexa Fluor 405/Cascade Blue dye |
| Dansyl-X, SE | Anti-dansyl ( |
| DNP-X, SE | Anti-DNP |
| DNP-X-biocytin-X, SE | |
| Fluorescein 5(6)-SFX | Anti-fluorescein/Oregon Green dye |
| Fluorescein-EX, SE | |
| Lucifer yellow iodoacetamide | Anti-lucifer yellow dye |
| Oregon Green 488-X, SE | Anti-fluorescein/Oregon Green dye |
| 5(6)-TAMRA-X, SE | Anti-tetramethylrhodamine, anti-Texas Red dye |
| Rhodamine Red-X, SE | Anti-tetramethylrhodamine, anti-Texas Red dye |
| Texas Red-X, SE | Anti-tetramethylrhodamine, anti-Texas Red dye |

As used herein, the term "multiplexed" refers to the detection of multiple signals (e.g., two or more signals), such as, for example, analytes, fluorescent signals, analog or digital signals, that are combined into one signal over a shared medium. The term encompasses the detection of multiple signals simultaneously in a single sample or single reaction vessel, as well as the combining of images of multiple signals to obtain one image that reflects the combination.

In certain embodiments, a detectable label such as a fluorophore is tethered to streptavidin via a cleavable linker. As used herein, the term "cleavable linker" refers to a linker that can be selectively cleaved to produce two products. Application of suitable cleavage conditions to a molecule containing a cleavable linker that is cleaved by the cleavage conditions will produce two byproducts. Cleavable linkers suitable for the detectable labels of this disclosure are preferably stable, e.g. to physiological conditions, until it is contacted with a cleavage-inducing stimulus, e.g., an agent such as a chemical, enzyme, or other cleavage-inducing agent such as light. Exemplary cleavable linkers include, without limitation, chemically cleavable linkers, photocleavable linkers, and enzymatically cleavable linkers. Other cleavable linkers appropriate for use in methods and compositions of this disclosure include, without limitation, structures cleaved by enzymes (e.g., enzymatically cleavable linkers), nucleophiles (e.g., nucleophilically cleavable linkers), electrophiles (e.g., electrophilically cleavable linkers), photo-irradiation (e.g., photocleavable linkers), metal catalysis (e.g., metal cleavable linkers), linkers that are cleavable under reductive or oxidative conditions (e.g., a disulfide linker or a diazobenzene linker), and linkers that are cleavable using an acidic reagent or a basic reagent. Preferably, the cleavable linker is a chemically cleavable linker. Chemically cleavable groups include azide and disulfide groups. Photocleavable linker groups include nitrobenzo groups. Enzyme-sensitive cleavable groups include amino, ester, and amide groups. In some embodiments, linkers that are cleavable by enzymes such as metalloproteinases and collagenases may be used.

As described herein, to enable fluorescence signal removal after protein staining, the detectably labeled streptavidin preferably comprises a fluorophore tethered to streptavidin through a chemically cleavable linker. An important aspect of the technology of this disclosure is efficient cleavage of the detectable label in a cellular environment while maintaining protein antigenicity. In preferred embodiments, the cleavable linker that satisfies these parameters is an azide-based linker or an allyl-based linker. Further examples of suitable linkers and cleavage mechanisms are described by Milton et al. (U.S. Pat. No. 7,414,116) and by Leriche et al. (*Bioorg. Med. Chem.*, 2012, 20:571-582), which are incorporated herein by reference in their entirety. The linker may be cleavable using a variety of approaches including the addition of a chemical agent, irradiation with one or more wavelengths of light, enzymatic reaction and the like.

In some embodiments, a cleavable fluorescent streptavidin comprises a cleavable Cy5 NHS ester. Cleavable Cy5 NHS ester can be prepared according to previously described methods (see, e.g., Mondal et al., *Angew. Chemie Int. Ed.* 2017, 56(10):2636-2639). In some cases, 1 nmol of cleavable Cy5 NHS ester and 2 µL of $NaHCO_3$ solution (1 M) are added to 20 µL of streptavidin solution at a concentration of 1 mg/mL. The mixture is preferably incubated under dark, room temperature conditions for about 15 minutes. The labeled streptavidin can be purified, for example, by using a size-exclusion spin chromatography column (e.g., a spin column comprising sized Bio-Gel® P gels).

Any appropriate detectable label can be used to produce a cleavable detectably-labeled streptavidin. In some cases, the detectable label of the cleavable detectably-labeled streptavidin is a fluorophore. In such cases, the cleavable detectably-labeled streptavidin is cleavable fluorescent streptavidin (CFS). Appropriate fluorophores for use in the methods of this disclosure include, without limitation, Cy5, TAMRA (labeled with tetramethylrhodamine or "TMR"), ALEXA FLUOR™ 594, and ATTO 647N and ATTO 700 fluorophores (ATTO-TEC, Germany). Other fluorophores appropriate for use according to the methods provided herein include, without limitation, quantum dots, ALEXA FLUOR™ 350, ALEXA FLUOR™ 532, ALEXA FLUO® 546, ALEXA FLUOR™ 568, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ DYES (e.g., DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800 and the like), Texas Red, and Cy2, Cy3.5, Cy5.5, and Cy7. In addition to the use of fluorophores as a detectable moiety, other labels such as luminescent agents (e.g., chemiluminescent agents), quantum dots, fluorescent proteins, and radioisotopes can also be used as detection tags.

The targeting agent will vary depending on the type of target biomolecule. In some embodiments, the target biomolecule is a protein or peptide. In such cases, the targeting agent will be an antibody that specifically binds to the target protein or peptide. For example, if the target biomolecule is protein Histone deacetylase 2 (HDAC2), the target agents comprise biotin-conjugated anti-HDAC2 antibodies. Antibodies suitable for the methods include, without limitation, polyclonal antibodies, monoclonal antibodies, and antigen-binding fragments thereof. Biotin-conjugated (e.g., biotinylated) antibodies can be used to detect other target biomolecules such as lipids and metabolites. Biotin-conjugated antibodies can be prepared by any appropriate method. For example, in some cases, biotin-conjugated antibodies are prepared by contacting a primary antibody solution to 3 nmol of NHS—SS-Biotin (succinimidyl 2-(biotinamido)-ethyl-1,3'-dithiopropionate) and 2 µL of $NaHCO_3$ solution (1 M). In some cases, the NHS—SS-Biotin is EZ-Link™ Sulfo-NHS—SS-Biotin (Thermo Fisher Scientific), which is a thiol-cleavable amine-reactive biotinylation reagent that contains an extended spacer arm to reduce steric hindrances associated with avidin binding. Cleavable hapten conjugated antibodies can be prepared similarly as the cleavable fluorescent streptavidin described here, using the synthesis protocol detailed by Mondal et al., *Angewandte Chemie International Edition* 56 (10), 2636-2639 (2017).

In other embodiments, the target biomolecule in a sample is a nucleic acid (e.g., DNA, RNA, peptide nucleic acid, locked nucleic acid, chemically modified oligonucleotide). In such cases, the targeting agent will be a biotin-conjugated oligonucleotide having sequence complementary to the target nucleic acid sequence. Under appropriate conditions, the biotin-oligonucleotide will hybridize to the target nucleic acid sequence. In some cases, multiple cycles of the method are performed to detect multiple target biomolecules using targeting agents that are biotin-conjugated antibodies, biotin-conjugated oligonucleotides, or a combination thereof.

In some embodiments, the target biomolecule is a carbohydrate. In such cases, the targeting agent can be a biotin-conjugated lectin that is capable of binding carbohydrate. As used herein, the term "lectin" refers to a protein or glycoprotein that binds to specific carbohydrate structures to form a lectin-carbohydrate complex. The term encompasses lectins derived from animal and plant sources, and which bind carbohydrates by affinity. The term "lectin" as used herein also encompasses glycoproteins and proteins not normally termed lectins but which immunologically bind carbohydrates, such as antibodies, e.g., monoclonal antibodies. Since lectins bind selectively to some but not all carbohydrates (e.g., monosaccharides, such as mannose, GlcNAc, gelatose, a-fructose or sialic acid) to different degrees, it will be understood that the type of lectin conjugated to biotin will vary depending on the target carbohydrate of interest.

In some cases, the "removing" or "cleaving" step comprises chemically cleaving the detectable label. Any appropriate means of removing a detectable signal or detectable label (e.g., a fluorophore) can be used according to the methods provided herein. Methods of removal can include without limitation photobleaching, chemical deactivation, chemical cleavage of the fluorophores (see the Examples below), enzymatic cleavage of the fluorophores, DNA/RNA strand displacement, chemical or heat denaturing of an intermediate fluorescent oligonucleotide, and the like. Since photobleaching can be a time-consuming step, in some cases the methods provided herein comprise efficiently removing fluorescence signals by chemical deactivation or chemical or enzymatic cleavage of detectable labels.

In some cases, chemical cleavage of biotin and/or fluorophores comprises incubating the contacted specimen with tris(2-carboxyethyl)phosphine (TCEP), followed by washing of the specimen in phosphate buffered saline comprising 0.1 Triton-X 100 (PBT) and/or phosphate buffered saline (PBS).

In some cases, the methods provided herein comprise chemical inactivation of fluorophores. For example, fluorophores can be inactivated by oxidation. Protocols for oxidation of dyes with hydrogen peroxide, which can be catalyzed using either acidic or basic conditions, or reactive oxygen species (ROS) are known to those practitioners in the art for changing the fluorescent properties of dyes and fluorescent proteins.

When fluorescently labeled streptavidin is used, fluorescence photomicroscopy can be used to detect and record the results of consecutive in situ analysis using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) *Science* 273:494; Roberts et al. (1999) *Genes Chrom. Cancer* 25:241; Fransz et al. (2002) *Proc. Natl. Acad. Sci. USA* 99:14584; Bayani et al. (2004) *Curr. Protocol. Cell Biol.* 22.5.1-22.5.25; Danilova et al. (2008) *Chromosoma* 117: 345; U.S. Pat. No. 6,066,459; and FISH TAG™ DNA Multicolor Kit instructions (Molecular probes) for a review of methods for painting chromosomes and detecting painted chromosomes.

To minimize issues of autofluorescence or background signal, oligonucleotide targeting agents can be designed to hybridize to a target nucleic acid at multiple places on the target nucleic acid sequence. Thus, an increased number of oligonucleotides will hybridize to each target nucleic acid sequence (e.g., transcript) to enhance signal to noise ratio. As used herein, the terms "binding," "to bind," "binds," "bound," or any derivation thereof refers to any stable, rather than transient, chemical bond between two or more molecules, including, but not limited to, covalent bonding, ionic bonding, and hydrogen bonding. The term "binding" encompasses interactions between polypeptides, for example, an antibody and its epitope on a target protein. The term also encompasses interactions between a nucleic acid molecule and another entity such as a nucleic acid or probe element. Specifically, binding, in certain embodiments, includes the hybridization of nucleic acids. In some cases, the methods further comprise a blocking step to reduce background signal. The term "blocking" as used herein refers to treatment of a sample with a composition that prevents the non-specific binding of the target substance to the sample. Typically a blocking composition comprises a protein, such as casein or albumin, and may additionally comprise surfactants. The function of the protein is to bind to the sample to prevent the non-specific binding of assay reagents.

In some cases, the method further comprises a washing step. For example, the method can further comprise washing to remove unhybridized targeting agents and non-specifically hybridized targeting agents following the second contacting step.

The methods of this disclosure can be performed using a tissue sample obtained from any biological entity. The term "biological entity" as used herein means any independent organism or thing, alive or dead, containing genetic material (e.g., nucleic acid) that is capable of replicating either alone or with the assistance of another organism or cell. Sources for nucleic acid-containing biological entities include, without limitation, an organism or organisms including a cell or cells, bacteria, yeast, fungi, algae, viruses, or a sample thereof. Specifically, an organism of the current disclosure includes bacteria, algae, viruses, fungi, and mammals (e.g., humans, non-human mammals). The methods and compositions described herein can be performed using a variety of biological or clinical samples comprising cells that are in any (or all) stage(s) of the cell cycle (e.g., mitosis, meiosis, interphase, G0, G1, S and/or G2). As used herein, the term "sample" include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. In some cases, samples are obtained by swabbing, washing, or otherwise collecting biological material from a non-biological object such as a medical device, medical instrument, handrail, door knob, etc. Samples are prepared for assays of this disclosure using conventional techniques, which typically depend on the source from which a sample or specimen is taken. These examples are not to be construed as limiting the sample types applicable to the methods and/or compositions described herein.

In some cases, the methods provided herein comprise a cell or tissue fixation step. For example, the cells of a biological sample (e.g., tissue sample) can be fixed (e.g., using formalin, formaldehyde, or paraformaldehyde fixation techniques known to one of ordinary skill in the art). In some cases, the tissue is formalin-fixed and paraffin-embedded (FFPE). Any fixative that does not affect antibody binding or nucleic acid hybridization can be utilized in according to the methods provided herein. In other cases, the methods are performed on unfixed ("fresh") tissue samples.

As described herein, the methods of the present invention provide for multiplexed in situ analysis of biomolecules in a tissue. Through consecutive cycles of targeting agent binding/hybridization, fluorescence imaging, and signal removal, different biomolecule species can be identified as fluorescent spots with unique color sequences.

As used herein, the term "biomolecule" or "biological molecule" refers to any molecule that is substantially of biological origin and encompasses proteins, peptides, and nucleic acids. Such molecules may include non-naturally occurring components that mimic a naturally occurring component, e.g., a non-naturally occurring amino acid. The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. As used herein, the terms "nucleic acid" or "oligonucleotide" refer to and encompass any physical string or collection of monomer units (e.g., nucleotides) that can connect to form a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), locked nucleic acids, other chemically modified nucleic acids, and the like. The nucleotides of the nucleic acid can be deoxyribonucleotides, ribonucleotides or nucleotide analogs, and can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The nucleic acid can additionally comprise non-nucleotide elements such as labels, quenchers, blocking groups, or the like. The nucleic acid can be single-stranded or double-stranded. It will be understood by practitioners in the art that natural oligonucleotides, synthetic oligonucleotides, peptide nucleic acids (PNA), locked nucleic acids (LNA), and other chemically modified nucleic acids are suitable for use as detection probes for target nucleic acids (e.g., DNA, RNA) of interest.

As used herein, the terms "nucleic acid of interest," and "target nucleic acid" include a nucleic acid originating from one or more biological entities within a sample. The target nucleic acid of interest to be detected in a sample can be a sequence or a subsequence from DNA, such as nuclear or mitochondrial DNA, or cDNA that is reverse transcribed from RNA in the sample. The sequence of interest can also be from RNA, such as mRNA, rRNA, tRNA, miRNA, siRNAs, antisense RNAs, or long noncoding RNAs. More generally, the sequences of interest can be selected from any combination of sequences or subsequences in the genome or transcriptome of a species or an environment. In some cases, a defined set of targeting agents are oligonucleotide probes that are designed to hybridize to the plurality of sequences that would be expected in a sample, for example a genome or transcriptome, or a smaller set when the sequences are known and well-characterized, such as from an artificial source.

Oligonucleotide probes useful for the methods provided herein are of any length sufficient to permit probe penetration and to optimize hybridization of probes for in situ analysis according to the methods of this disclosure. Preferably, probe length is about 20 bases to about 500 bases. As probe length increases, so increases the number of binding sites that can be incorporated into a given probe for hybridization to the probe of the following cycle as well as the signal to noise ratio. However, longer than 500 bases, the probes may not efficiently penetrate the cellular membrane. Preferably, the oligonucleotide probes have a probe length between 20 and 500 nucleotides, 20 and 250, 50 and 250, 150 and 250 nucleotides, 20 and 150, or 50 and 150 nucleotides, inclusive.

The terms "hybridize" and "hybridization" as used herein refer to the association of two nucleic acids to form a stable duplex. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, N.Y.). One of skill in the art will understand that "hybridization" as used herein does not require a precise base-for-base complementarity. That is, a duplex can form, between two nucleic acids that contained mismatched base pairs. The conditions under which nucleic acids that are perfectly complementary or that contain mismatched base pairs will hybridize to form a duplex are well known in the art and are described, for example, in MOLECULAR CLONING: A LABORATORY MANUAL, 3$^{rd}$ ed., Sambrook et al., eds., Cold Spring Harbor Press, Cold Spring Harbor (2001) at Chapter 10, which is herein incorporated by reference. As used herein, the term "complementary" refers to a nucleic acid that forms a stable duplex with its "complement". For example, nucleotide sequences that are complementary to each other have mismatches at less than 20% of the bases, at less than about 10% of the bases, preferably at less than about 5% of the bases, and more preferably have no mismatches.

Kits

In another aspect, provided herein is a kit comprising reagents for performing multiplexed in situ analysis of biomolecules in a tissue. Preferably, the kit comprises a cleavable detectably-labeled streptavidin and a written insert component comprising instructions for performing multiplexed in situ analysis of target biomolecules according to the methods provided herein. In some cases, the detectable label is a fluorophore (e.g., Cy5, TAMaRA, ALEXA FLUOR™ 594, ATTO 647N, ATTO 700). In some cases, the kit further comprises a one or more biotin-conjugated targeting agents configured to bind or hybridize to a target biomolecule. As described herein, the targeting agents can be synthetic DNA oligonucleotide probes, polyclonal antibodies, monoclonal antibodies, antigen-binding fragments of an antibody, or some combination thereof. In some cases, the plurality of biotin-conjugated targeting agents comprises biotin-conjugated synthetic DNA oligonucleotide probes. In some cases, the plurality of biotin-conjugated targeting agents comprises biotin-conjugated polyclonal or monoclonal antibodies, or antigen-binding fragments thereof. In some cases, the kit further comprises an amplification reaction buffer, a blocking reagent, and/or a hydrogen peroxide additive.

A kit will preferably include instructions for employing the kit components as well the use of any other reagent not included in the kit. Instructions may include variations that can be implemented. In some cases, the kit further comprises tris(2-carboxyethyl)phosphine (TCEP) or another agent for removing the detectable label from streptavidin. In such cases, the written instruction component further comprises instructions for removing the detectable label from the detectably-labeled streptavidin using the TCEP or other removing agent.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As used herein and in the appended claims, the singular forms "a", "an" and "the" include plural reference, unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. In addition, the terms "comprising", "including" and "having" can be used interchangeably.

As used herein, "about" means within 5% of a stated concentration range or within 5% of a stated time frame.

Various embodiments and aspects of the present invention as delineated hereinabove and as claimed in the claims section below find experimental support in the following examples which, together with the above descriptions, illustrate some embodiments of the invention in a non-limiting fashion.

EXAMPLES

Example 1: Highly Sensitive and Multiplexed In Situ Protein Profiling with Cleavable Fluorescent Streptavidin (CFS)

This example demonstrates a highly sensitive and multiplexed in situ protein analysis approach using cleavable biotin labeled primary antibodies and cleavable fluorescent streptavidin (CFS). In this approach, protein targets are sensitively detected by cleavable biotin conjugated antibodies and cleavable fluorescent streptavidin (CFS) using a layer-by-layer signal amplification method. Through reiterative cycles of protein labeling, fluorescence imaging and signal removal, comprehensive protein profiling can be achieved in individual cells at the optical resolution.

Materials and Methods

Chemicals and solvents were purchased from Sigma-Aldrich or TCI America, used directly without further purification, unless otherwise noted. Bioreagents were purchased from Invitrogen, unless otherwise indicated.

Protein Staining with Cleavable Fluorescent Streptavidin (CFS) in Cells

Cell Culture

HeLa CCL-2 cells (ATCC) were maintained in Dulbelcco's modified Eagle's Medium (DMEM) supplemented with 10% fetal bovine serum, 100 U/mL penicillin and 100 g/mL streptomycin in a humidified atmosphere at 37° C. with 5% $CO_2$. Cells were plated on chambered coverglass (0.2 ml medium/chamber) (Thermo Fisher Scientific) and allowed to reach 60% confluency in 1-2 days.

Cell Fixation and Permeabilization

Cultured HeLa CCL-2 cells were fixed with 4% formaldehyde (Polysciences) in 1×PBS at 37° C. for 15 minutes, followed by washing with 1×PBS, 3×5 minutes. Cells were then permeabilized with PBT (0.1% Triton-X 100 in Ix PBS) for 10 minutes at room temperature, and subsequently washed 3 times with 1×PBS, each for 5 minutes.

Preparation of Cleavable Fluorescent Streptavidin

Cleavable Cy5 NHS ester was prepared according to Mondal et al. (*Angew. Chemie Int. Ed.* 2017, 56, 2636-2639). To 20 µL of streptavidin solution at a concentration of 1 mg/mL, 1 nmol of cleavable Cy5 NHS ester and 2 µL of $NaHCO_3$ solution (1 M) was added. The mixture was incubated in dark and room temperature for 15 min. The labeled streptavidin was purified by p-6 biogel column.

Preparation of Biotin-SS-Ab

To 20 µL of primary antibody solution at a concentration of 1 mg/mL, 3 nmol of EZ link Sulfo-NHS—SS-Biotin (Thermo Fisher Scientific) and 2 µL of $NaHCO_3$ solution (1 M) was added. The mixture was incubated in dark and room temperature for 15 min, and then the conjugation product was purified by p-6 biogel column.

Immunofluorescence with CFS

Fixed HeLa cells were incubated with antibody blocking buffer (10% normal goat serum (v/v), 1% bovine serum albumin (w/v), 0.1 Triton-X 100 in 1×PBS) for 1 h at room temperature, and then washed 3 times with PBT, each for 5 minutes (min). To block the cell endogenous biotin, the cells were treated with 0.1 mg/mL streptavidin in 1×PBS for 15 min at room temperature, and washed 3 times with 1×PBS, each for 5 min. Subsequently, the cells were incubated with 0.5 mg/mL biotin in 1×PBS for 30 min at room temperature, and washed with 1×PBS 3 times, each for 5 min. After blocking, the cells were incubated with Biotin-SS-Ab in antibody blocking buffer (concentration varies and suggested by manufacturers) for 45 min at room temperature, and washed with PBT for 3 times, each for 10 min. Subsequently, the cells were incubated with 10 µg/mL cleavable fluorescent streptavidin in 1% BSA in PBT for 30 min, and washed 3 times with 1×PBS, each for 5 min. The cells were washed with GLOX buffer (0.4% glucose and 10 mM Tris HCl in 2×SSC) for 1-2 min at room temperature, and then imaged in GLOX solution (0.37 mg $mL^{-1}$ glucose oxidase and 1% catalase in GLOX buffer).

Signal Amplification

To amplify the staining signal, the cells were incubated with cleavable biotin conjugated goat anti-chicken antibodies (Thermo Fisher Scientific) in 1% BSA in PBT at a concentration of 10 µg/mL for 30 min, and then washed 3 times with 1×PBS, each for 5 min. Afterwards, the cells were incubated with cleavable fluorescent streptavidin in 1% BSA in PBT at a concentration of 10 µg/mL, and again washed 3 times with 1×PBS, each for 5 min. Multiple amplification cycles can be repeated to obtain the desired signal intensity.

Fluorophore and Biotin Cleavage

Fluorophore and biotin cleavage was performed by incubating the specimen with tris(2-carboxyethyl)phosphine (TCEP, pH=9.5, 100 mM in deionized water) for 30 min at 37° C. Subsequently, the cells were washed 3 times with PBT and 3 times with 1×PBS, each for 5 min.

Streptavidin Blocking

After cleavage, the cells were incubated with 0.5 mg/mL biotin in 1×PBS for 30 min at room temperature, and then washed 3 times with 1×PBS, each for 5 min.

Quantification of the Fluorophore Cleavage Efficiency

Fixed and blocked HeLa CCL-2 cells were incubated with 10 µg/mL cleavable biotin labeled rabbit anti-Ki67 (Thermo Fisher Scientific) for 45 min. Subsequently, the cells were stained by 10 µg/mL cleavable fluorescent streptavidin. Then, one, two, three and four rounds of amplification were applied to different sets of cells. In each round of amplification, the cells were first incubated with cleavable biotin labeled goat-anti-chicken antibodies and then with cleavable fluorescent streptavidin. The cells were then incubated with TCEP (100 mM, pH=9.5) for 30 min at 37° C. Subsequently, the cells were washed 3 times with PBT and 3 times with 1×PBS, each for 5 min.

Quantification of the Streptavidin Blocking Efficiency

Fixed and blocked HeLa CCL-2 cells were incubated with 10 µg/mL cleavable biotin labeled rabbit anti-Ki67 (Thermo Fisher Scientific) for 45 min. Subsequently, cells were stained by 10 µg/mL cleavable fluorescent streptavidin. Following that, one, two, three and four rounds of amplification were applied to different sets of cells. In each round of amplification, the cells were first incubated with cleavable biotin labeled goat-anti-chicken antibodies and then with cleavable fluorescent streptavidin. Biotin and fluorophores were cleaved by TCEP (100 mM, pH=9.5). The cells were blocked with 0.5 mg/mL biotin. The cells were incubated with cleavable biotin labeled goat anti-chicken and then cleavable fluorescent streptavidin Multiplexed Protein Analysis in HeLa Cells Fixed and blocked HeLa CCL-2 cells were incubated with 10 µg/mL cleavable biotin labeled primary antibodies. Subsequently, cells were stained by 10 µg/mL cleavable fluorescent streptavidin. One to three amplification cycles were applied. In each amplification cycle, cells were first incubated with cleavable biotin labeled goat anti-chicken antibodies (Thermo Fisher Scientific) and then cleavable fluorescent streptavidin. After imaging, cells were incubated with TCEP (100 mM, pH=9.5) to cleave the fluorophores and biotin. Cells were then blocked with 50 mM iodoacetamide, 0.1 mg/mL streptavidin and 0.5 mg/mL biotin, followed by the next immunofluorescence cycle. Rabbit anti-c-erbB-2 (Thermo Fisher Scientific), rabbit anti-Ki67 (Thermo Fisher Scientific), and rabbit anti-Histone H4 (mono methyl K20) (Abcam) were used as primary antibodies.

Conventional Immunofluorescence

Fixed and blocked HeLa CCL-2 cells were incubated with 10 µg/mL Cy5 labeled or unconjugated primary antibodies. Subsequently, cells were stained by 10 µg/mL Cy5 labeled goat anti-rabbit secondary antibodies (Thermo Fisher Scientific). Rabbit anti-c-erbB-2, rabbit anti-Ki67, and rabbit anti-Histone H4 (mono methyl K20) were used as primary antibodies. Cy5 labeled rabbit anti-Ki67 was prepared according to the literature [16].

Protein Staining in a Brain FFPE Tissue

Deparaffinization and Antigen Retrieval of FFPE Tissues

A brain FFPE tissue slide was deparaffinized in xylene for 3 times, 10 min for each. Then the slide was immersed in 100% ethanol for 2 min, 95% ethanol for 1 min, 70% ethanol for 1 min, 50% ethanol for 1 min, 30% ethanol for 1 min. The slide was rinsed with deionized water. Afterwards, a combination of 'heat induced antigen retrieval' (HIAR) and 'enzymatic antigen retrieval' was used. HIAR was done using a pressure cooker (Cuisinart). The slide was immersed in antigen retrieval buffer (10 mM sodium citrate, 0.05% Tween 20, pH=6.0), and water-bathed in pressure cooker for 20 min with the 'High pressure' setting. Subsequently, the slide was rinsed 3 times with 1×PBS, each for 5 min. The slide were treated with pepsin digest-all 3 (Life Technologies) for 10 min, and then washed 3 times with 1×PBS, each for 5 min.

Protein Staining in FFPE Tissues

To block the endogenous biotin, the slide was treated with 0.1 mg/mL streptavidin in 1×PBS for 15 min at room temperature, and washed 3 times with 1×PBS, each for 5 min. Subsequently, the slide were incubated with 0.5 mg/mL biotin in 1×PBS for 30 min at room temperature, and washed 3 times with 1×PBS, each for 5 min. The slide was incubated with 10 µg/mL cleavable biotin labeled rabbit anti-H3K4me3 (Cells Signaling) in antibody blocking buffer for 45 min, and washed 3 times with PBT, each for 10 min. The slide was stained by 10 µg/mL cleavable fluorescent streptavidin for 30 min, and then washed 3 times with 1×PBS, each for 5 min. Two cycles of amplification were applied. In each round of amplification, the cells were first incubated with cleavable biotin labeled goat-anti-chicken antibodies and then with cleavable fluorescent streptavidin. After imaging, the slide was incubated with TCEP (100 mM, pH=9.5) for 30 min at 37° C., and washed 3 times with PBT and 3 times with 1×PBS, each for 5 min. Streptavidin was blocked with 0.5 mg/mL Biotin. The tissue was restained with 10 µg/mL cleavable biotin labeled goat anti-chicken and then 10 µg/mL cleavable fluorescent streptavidin.

Imaging and Data Analysis

Stained cells and brain FFPE tissue were imaged under a Nikon Ti-E epifluorescence microscope equipped with 20× objective. Images were captured using a CoolSNAP HQ2 camera and Chroma filter 49009. Image data was analyzed with NIS-Elements Imaging software.

Results

As illustrated in FIG. 1, each staining cycle comprises five major steps. First, proteins of interest are targeted by cleavable biotin labeled primary antibodies and cleavable fluorescent streptavidin (CFS). Second, the specimen is incubated with a cleavable biotin labeled orthogonal antibody followed by CFS. This layer-by-layer signal amplification step can be repeated several times to achieve the desired signal intensities. Third, the specimen is imaged to generate quantitative single-cell protein expression profiles. Fourth, the fluorophores and the biotins unbound to streptavidin are efficiently removed by chemical cleavage. Finally, the leftover streptavidin is blocked with biotin. Through reiterative cycles of staining, amplification, imaging, cleavage and streptavidin blocking, a large number of proteins expressed with a wide range of expression levels can be characterized in single cells in situ.

To demonstrate the feasibility of this approach, biotin was conjugated to antibodies through a disulfide bond based cleavable linker and Cy5 to streptavidin through an azide based cleavable linker, according to previously described method. In this way, both biotin and Cy5 can be simultaneously removed by the reducing reagent tris(2-carboxyethyl)-phosphine (TCEP).

Figures 2A, 2B:
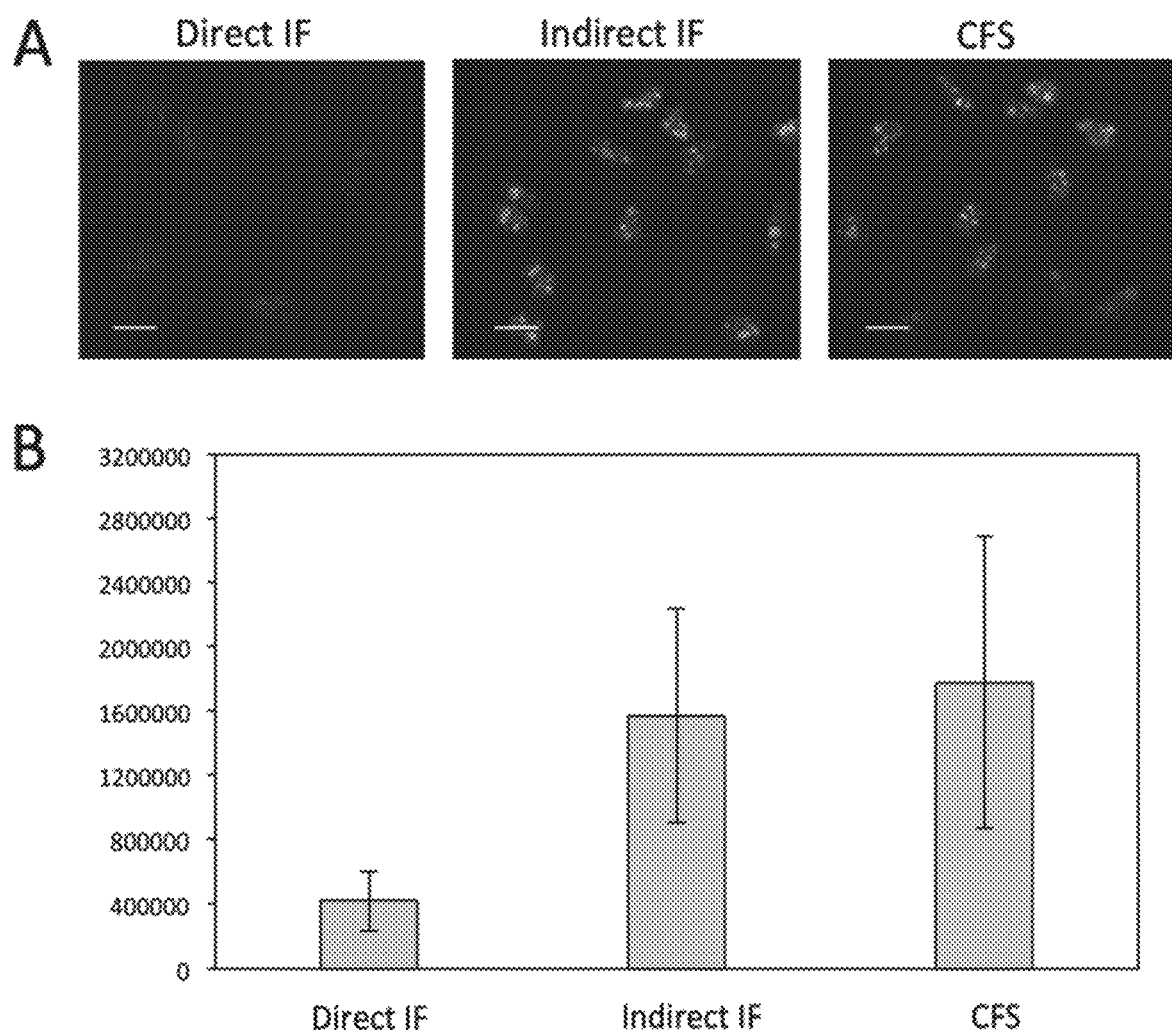
FIGS. 2A-2B. (A) Fluorescent images of protein Ki67 stained with direct IF, indirect IF, and cleavable fluorescent streptavidin (CFS). (B) Comparison of the averaged signal integration in single cells (n=30) for the 3 methods. Scale bars, 20 μm.
Figures 3A, 3B, 3C:
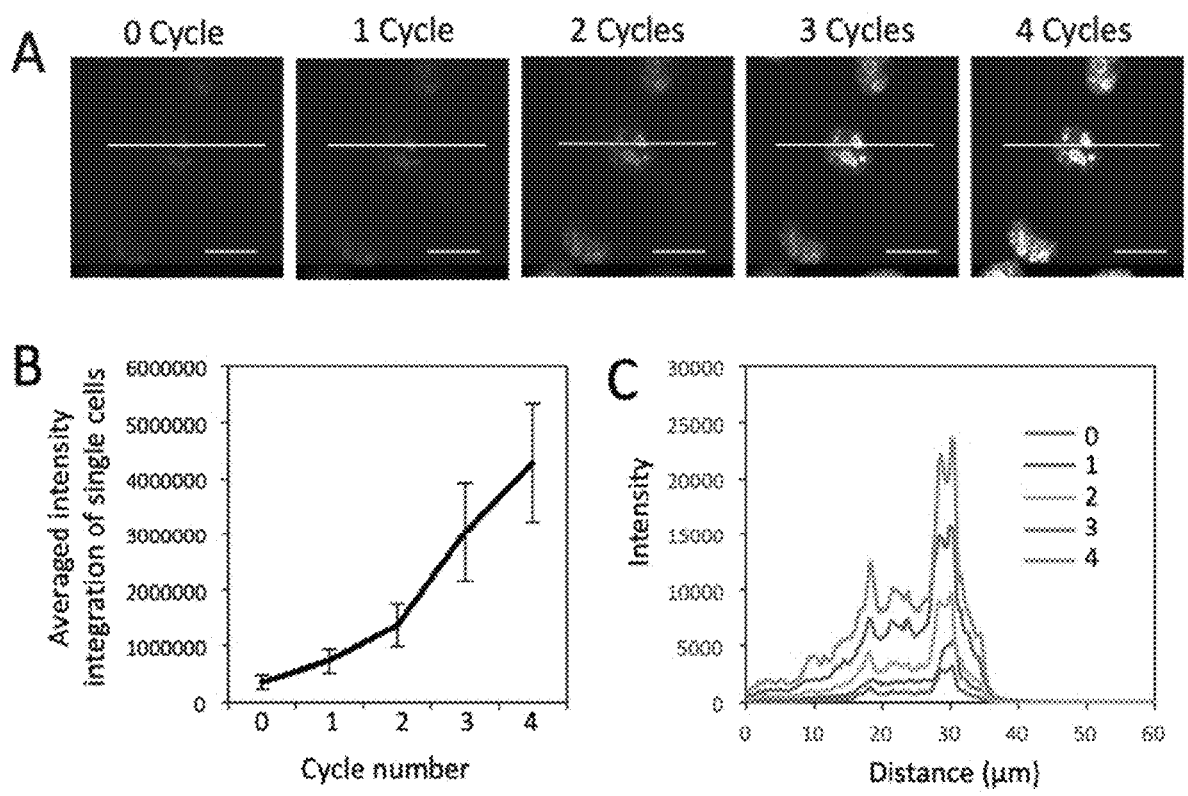
FIGS. 3A-3C. (A) Fluorescent images of protein Ki67 stained with 0 to 4 amplification cycles in HeLa cells. (B) Averaged signal integration in single cells (n=30) in amplification cycles 0 to 4. Error bars, standard deviation. (C) Fluorescence intensity profiles corresponding to the indicated line positions in amplification cycles 0 to 4. Scale bars, 20 μm.

Next, the detection sensitivity was evaluated by comparing it with direct and indirect immunofluorescence. Protein Ki67 in HeLa cells was stained with these 3 methods with the same concentration of primary antibodies (FIGS. 2A-2B). Compared with direct and indirect immunofluorescence, the CFS method does not lose the staining resolution (FIG. 2A). Without any signal amplification steps, the CFS method is ~4.5 times more sensitive than direct immunofluorescence and is comparable to indirect immunofluorescence (FIG. 2B). With 4 rounds of signal amplification, the original staining intensities were further increased by more than 10 times (FIGS. 3A-3C). These results demonstrate that our approach enhances the detection sensitivity of the existing in situ proteomics methods by at least one order of magnitude.

Figures 4A, 4B:
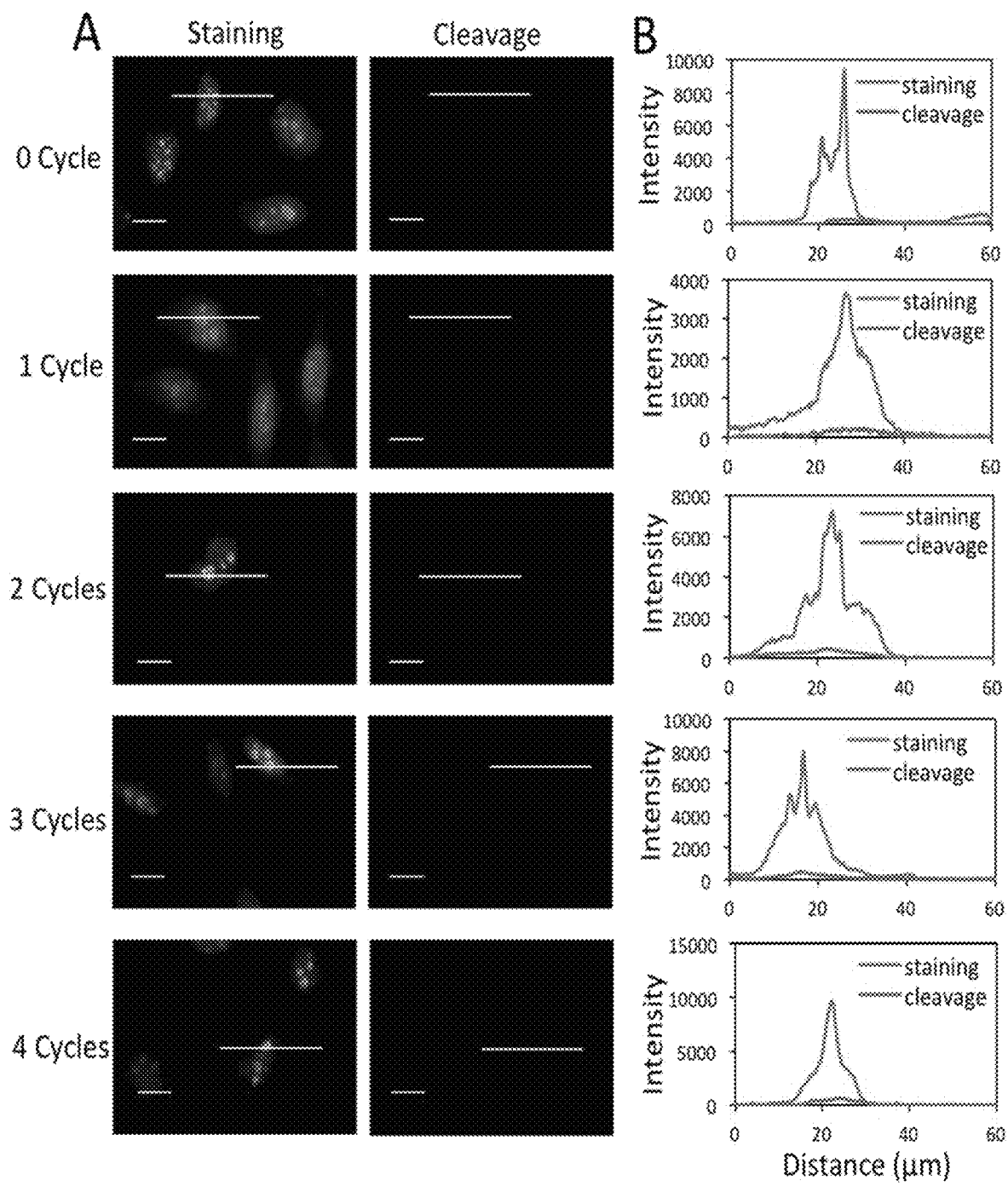
FIGS. 4A-4B. (A) Fluorescent images of protein Ki67 stained with 0 to 4 amplifications cycles in HeLa cells and those after cleavage. The exposure time in amplification cycles 0 to 4 is 1 second (s), 500 milliseconds (ms), 250 ms, 125 ms, 62 ms, respectively. (B) Fluorescence intensity profiles corresponding to the indicated line positions in amplification cycles 0 to 4. Scale bars, 20 μm.
Figures 5A, 5B:
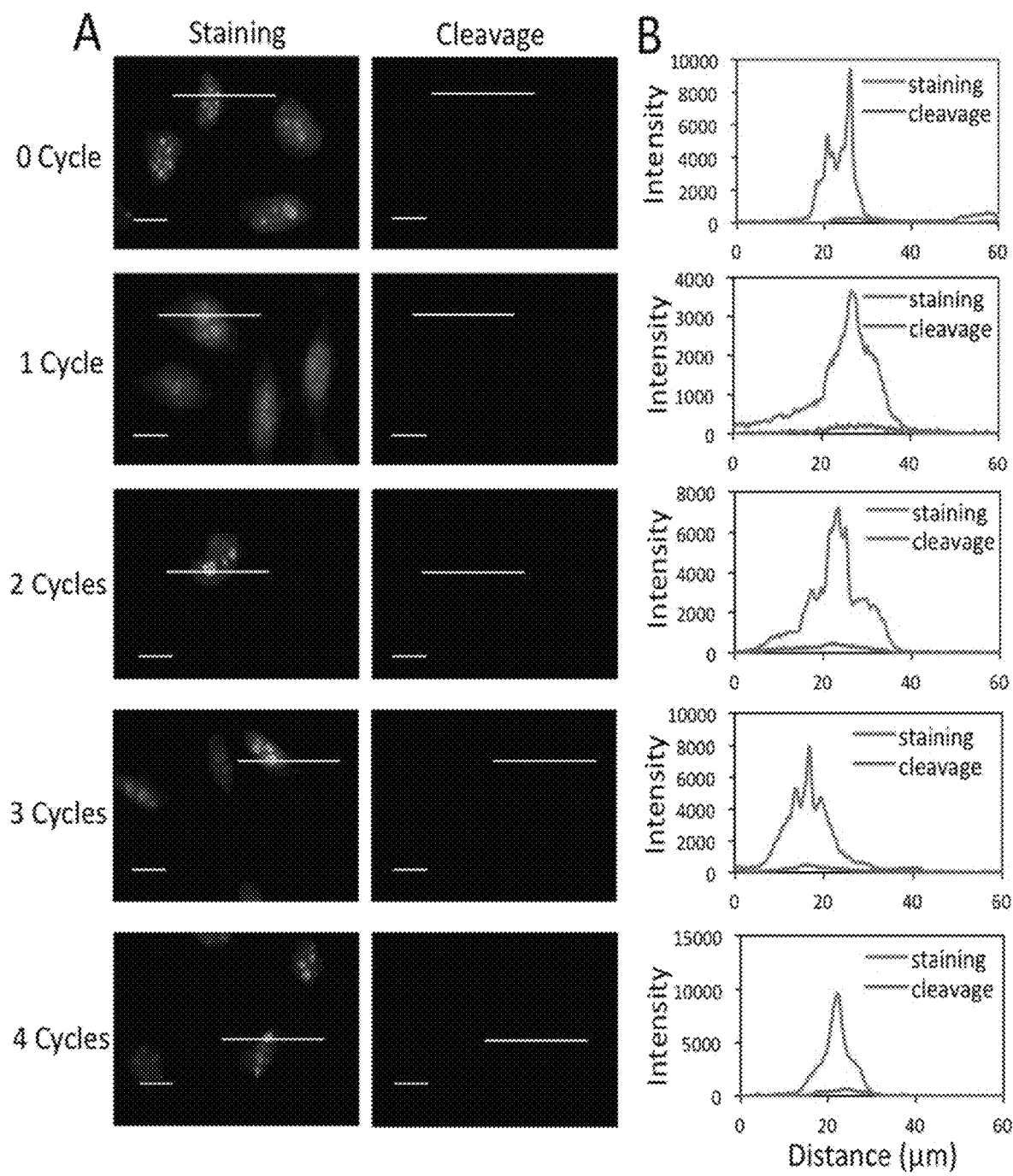
FIGS. 5A-5B. (A) Fluorescent images of protein Ki67 stained with 0 to 4 amplifications cycles in HeLa cells, after cleavage, and restained with CFS. The exposure time in amplification cycles 0 to 4 is 1 s, 500 ms, 250 ms, 125 ms, 62 ms, respectively. (B) Fluorescence intensity profiles corresponding to the indicated line positions in amplification cycles 0 to 4. Scale bars, 20 μm.
Figures 6A, 6B:
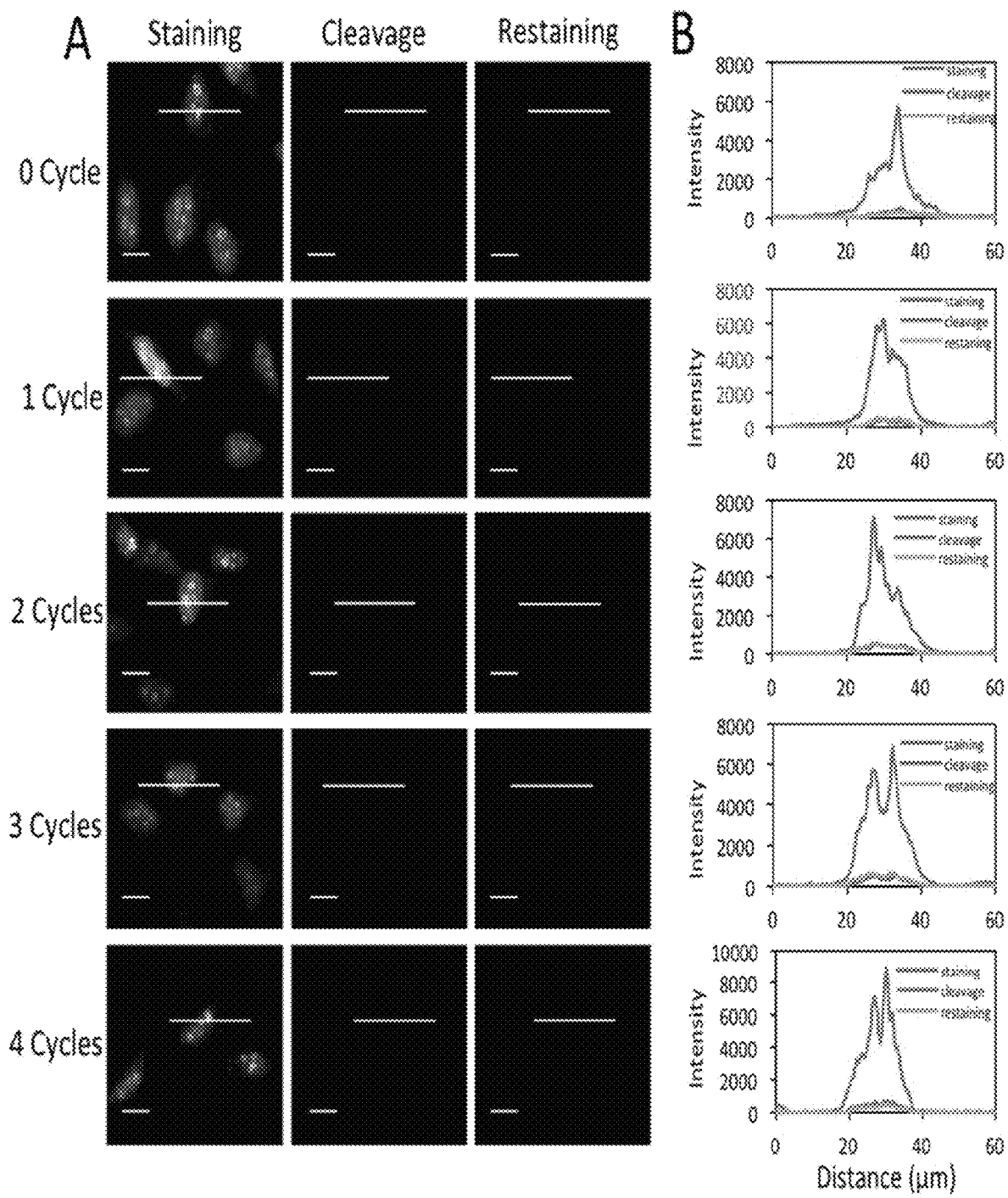
FIGS. 6A-6B. (A) Fluorescent images of protein Ki67 stained with 0 to 4 amplifications cycles in HeLa cells and those after cleavage. Following streptavidin blocking, the cells were restained with cleavable biotin-labeled orthogonal antibodies and CFS. The exposure time in amplification cycles 0 to 4 is 1 s, 500 ms, 250 ms, 125 ms, 62 ms, respectively. (B) Fluorescence intensity profiles corresponding to the indicated line positions in amplification cycles 0 to 4. Scale bars, 20 μm.

To enable multiplexed protein analysis by reiterative analysis cycles, three major requirements exist. (1) Fluorescence signals need to be efficiently erased by chemical cleavage. (2) The biotin not bounded to streptavidin has to be efficiently removed to avoid false positive signals in the next staining cycle. (3) Streptavidin needs to be efficiently blocked before the next staining cycle. To assess whether these three requirements are met by the CFS approach, protein Ki67 was stained with 0 to 4 amplification cycles in HeLa cells (FIG. 4A), and the cleavage efficiency (FIG. 4B) was quantified. After TCEP incubation, ~95% of signal was removed regardless of the number of the amplification rounds. To test whether the biotin unbounded to streptavidin can be removed by TCEP, we stained protein Ki67 with 0 to 4 amplification cycles (FIGS. 5A-5B). After TCEP cleavage, the cells were incubated with the CFS, again. No further fluorescence signal enhancement was introduced, suggesting that the free biotin is efficiently removed during the cleavage step. To evaluate the streptavidin blocking efficiency, protein Ki67 was stained with 0 to 4 amplification cycles (FIGS. 6A-6B). Subsequently, the cells were incubated with TCEP and then with biotin to block streptavidin. Another round of signal amplification was applied and no further fluorescence signal enhancement was detected. These results indicate that streptavidin is efficiently blocked by biotin.

Figures 7A, 7B, 7C, 7D:
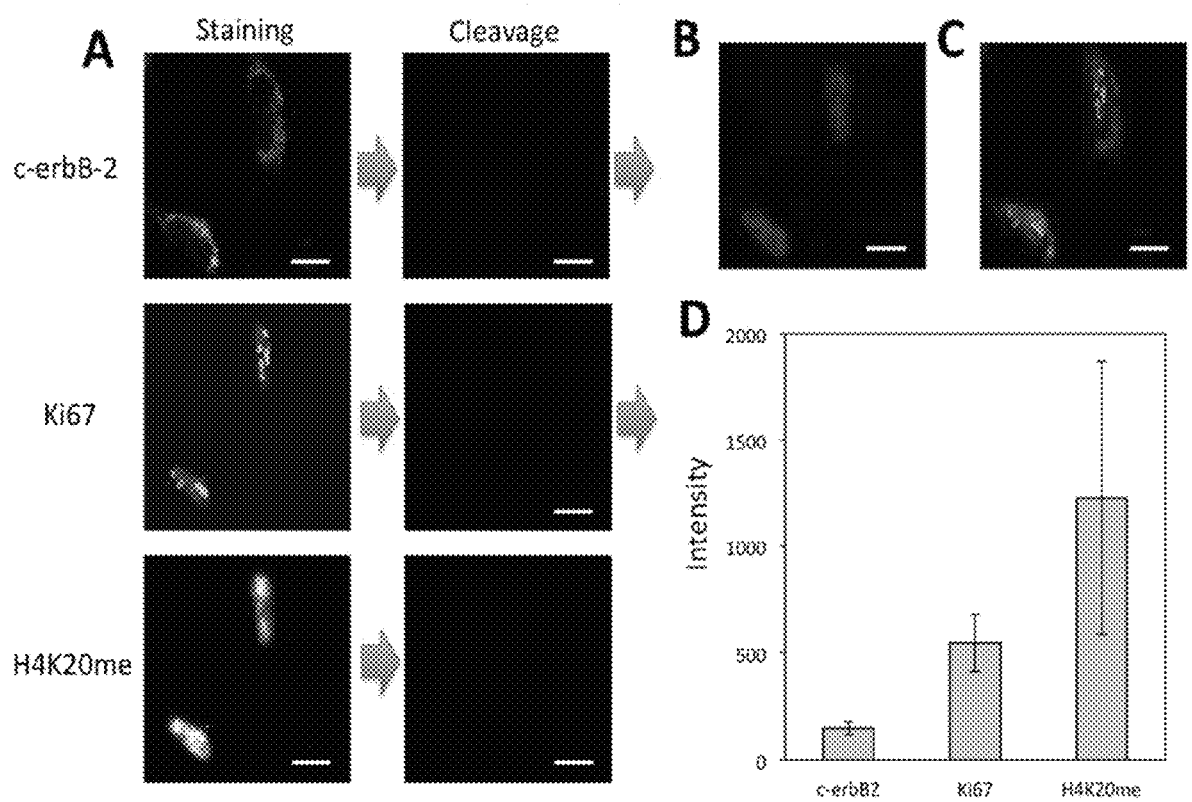
FIGS. 7A-7D. (A) Protein c-erbB-2, Ki67, and H4K20me were detected with CFS through reiterative staining cycles in the same set of HeLa cells. (B) Nuclei were stained with DAPI. (C) Digital overlay of the three staining images in (A). (D) Staining intensity (n=40) for the three proteins. Scale bars, 20 μm.

To demonstrate the feasibility of applying the CFS method for multiplexed protein analysis, proteins c-erbB-2, Ki67 and H4K20me were labeled through reiterative staining cycles in the same set of HeLa cells (FIGS. 7A-7B). The staining signals generated in the previous cycles do not reappear in the following cycles, confirming that the fluorophore and free biotin are efficiently cleaved and streptavidin is efficiently blocked. These three proteins were also stained by conventional immunofluorescence (FIGS. 10A-10F). The staining results obtained by this approach and by conventional immunofluorescence closely resemble each other. These results suggest that the CFS method enables the multiplexed protein profiling in single cells in situ.

Figures 8A, 8B, 8C, 8D:
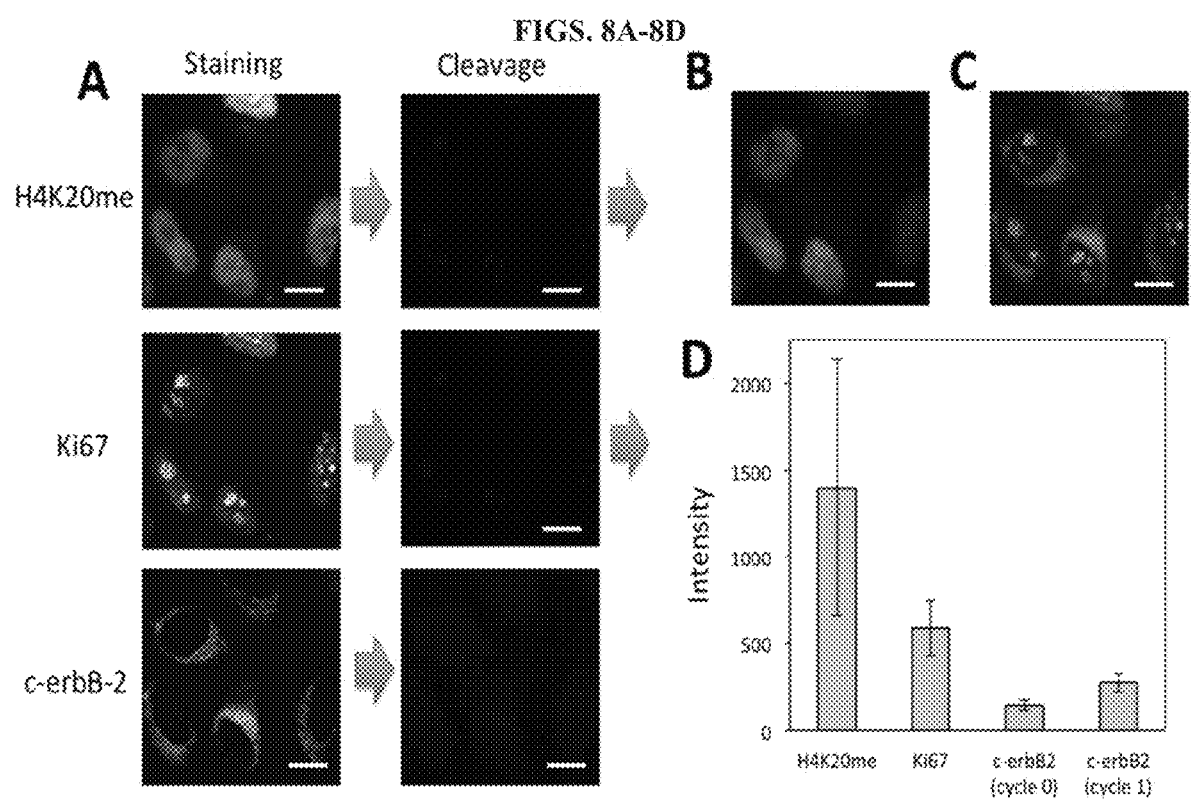
FIGS. 8A-8D. (A) H3K4me3 and Ki67 were detected with CFS through reiterative staining cycles without signal amplification. Afterwards, protein c-erbB-2 was detected by signal amplification with CFS in the same set of HeLa cells. (B) Nuclei were stained with DAPI. (C) Digital overlay of the three staining images in (A). (D) Staining intensity (n=40) for the three proteins. Scale bars, 20 µm.
Figures 9A, 9B, 9C, 9D, 9E, 9F:
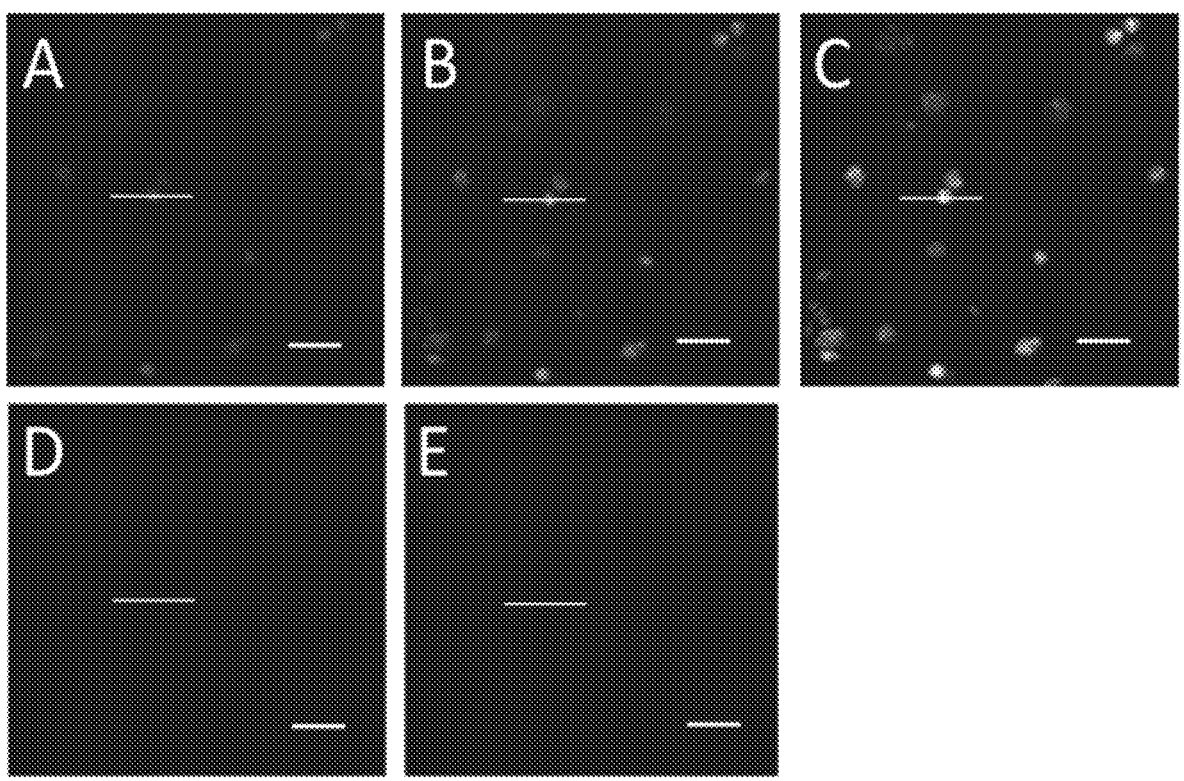
FIGS. 9A-9F. Protein H3K4me3 in a human FFPE brain tissue was stained with CFS in amplification cycles 1 (A), 2 (B), and 3 (C). (D) Afterwards, the stained tissue was incubated with TCEP. (E) Following chemical cleavage and streptavidin blocking, the tissue was incubated with cleavable biotin-conjugated antibodies and CFS again. (F) Fluorescence intensity profiles corresponding to the indicated line positions in (A) to (E). Scale bars, 25 µm.
Figures 10A, 10B, 10C, 10D, 10E, 10F:
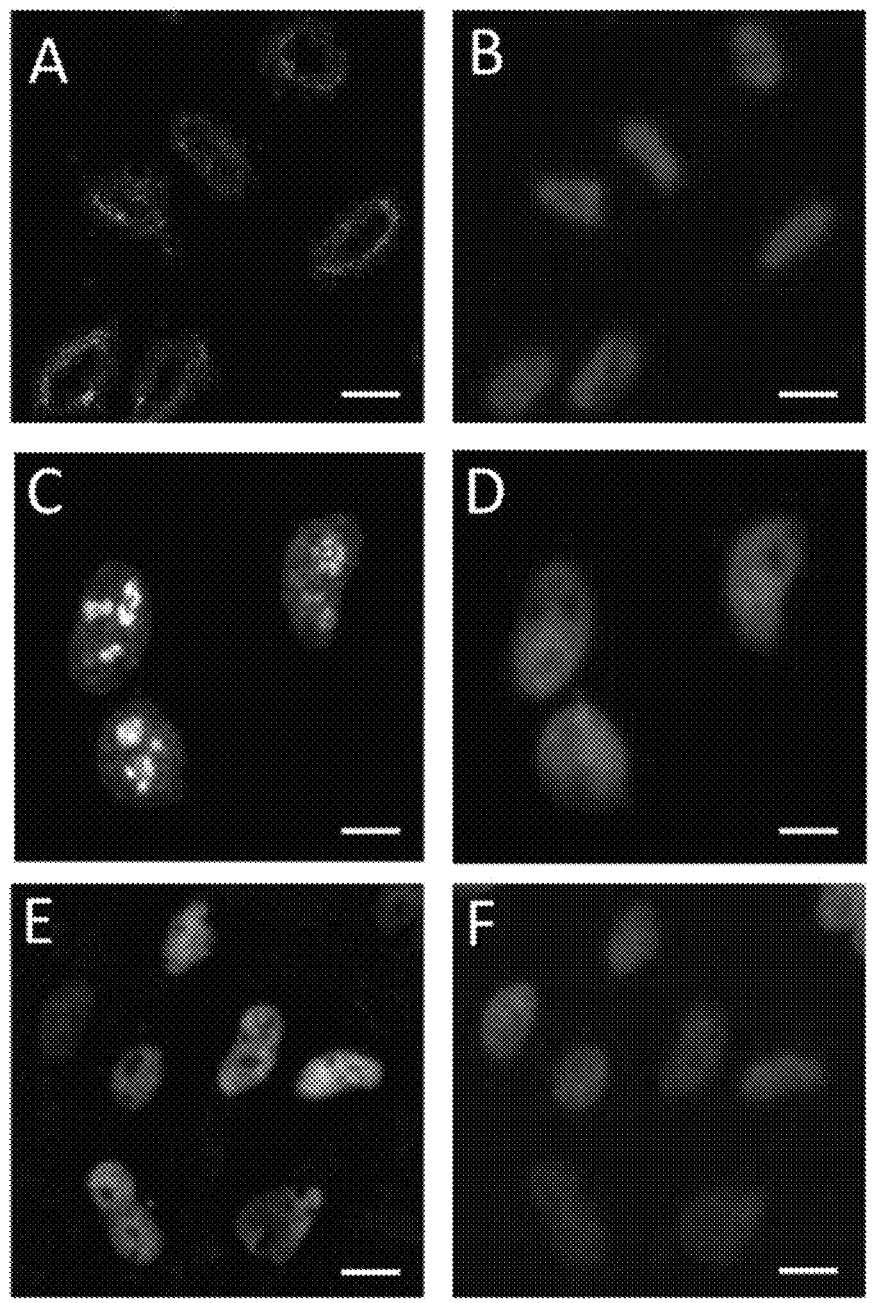
FIGS. 10A-10F. (A) Fluorescent image of protein c-erbB-2 in HeLa cells by conventional immunofluorescence and (B) the corresponding DAPI staining of nuclei. (C) Fluorescent image of protein Ki67 in HeLa cells by conventional immunofluorescence and (D) the corresponding DAPI staining of nuclei. (E) Fluorescent image of protein H4K20me in HeLa cells by conventional immunofluorescence and (F) the corresponding DAPI staining of nuclei. Scale bars, 20 µm.
Figure 11:
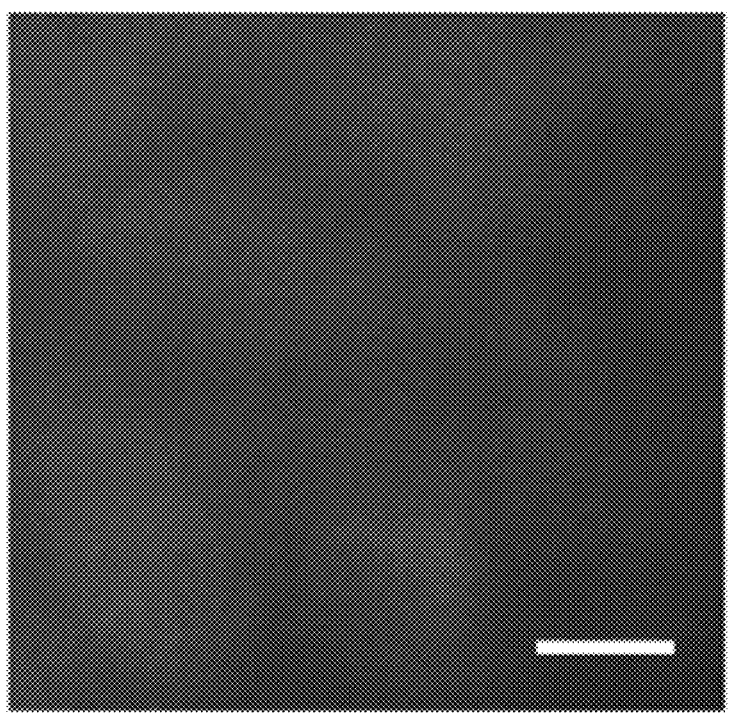
FIG. 11. Fluorescent image of protein c-erbB-2 stained in the third analysis cycle without signal amplification. Scale bar, 20 µm.
Figure 12A:
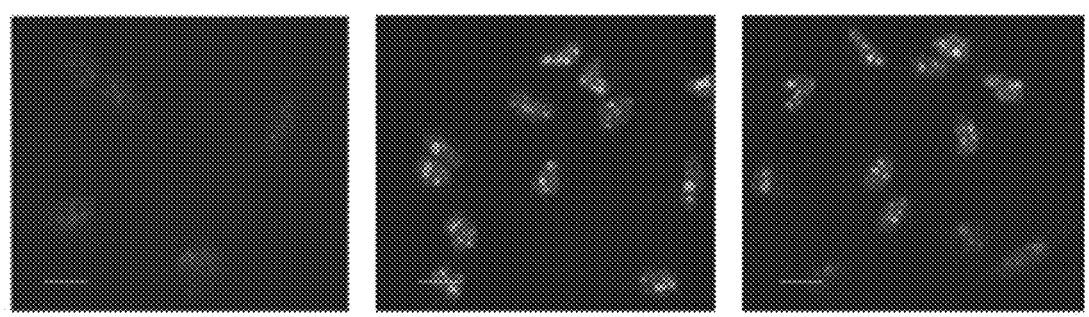
FIGS. 12A-12B. (A) Fluorescent images of protein Ki67 stained with direct immunofluorescence (IF) (left), indirect IF (middle), and cleavable fluorescent streptavidin (CFS). (B) Comparison of normalized staining intensity (n=30) for 3 methods. Scale bars, 20 µm.
Figure 12B:
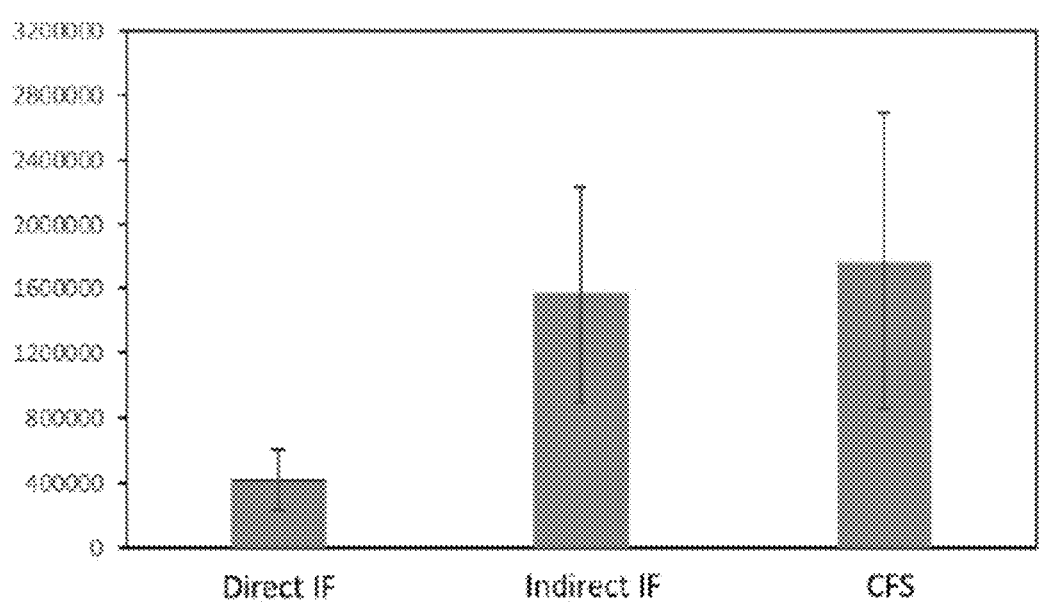
Figures 13A, 13B:
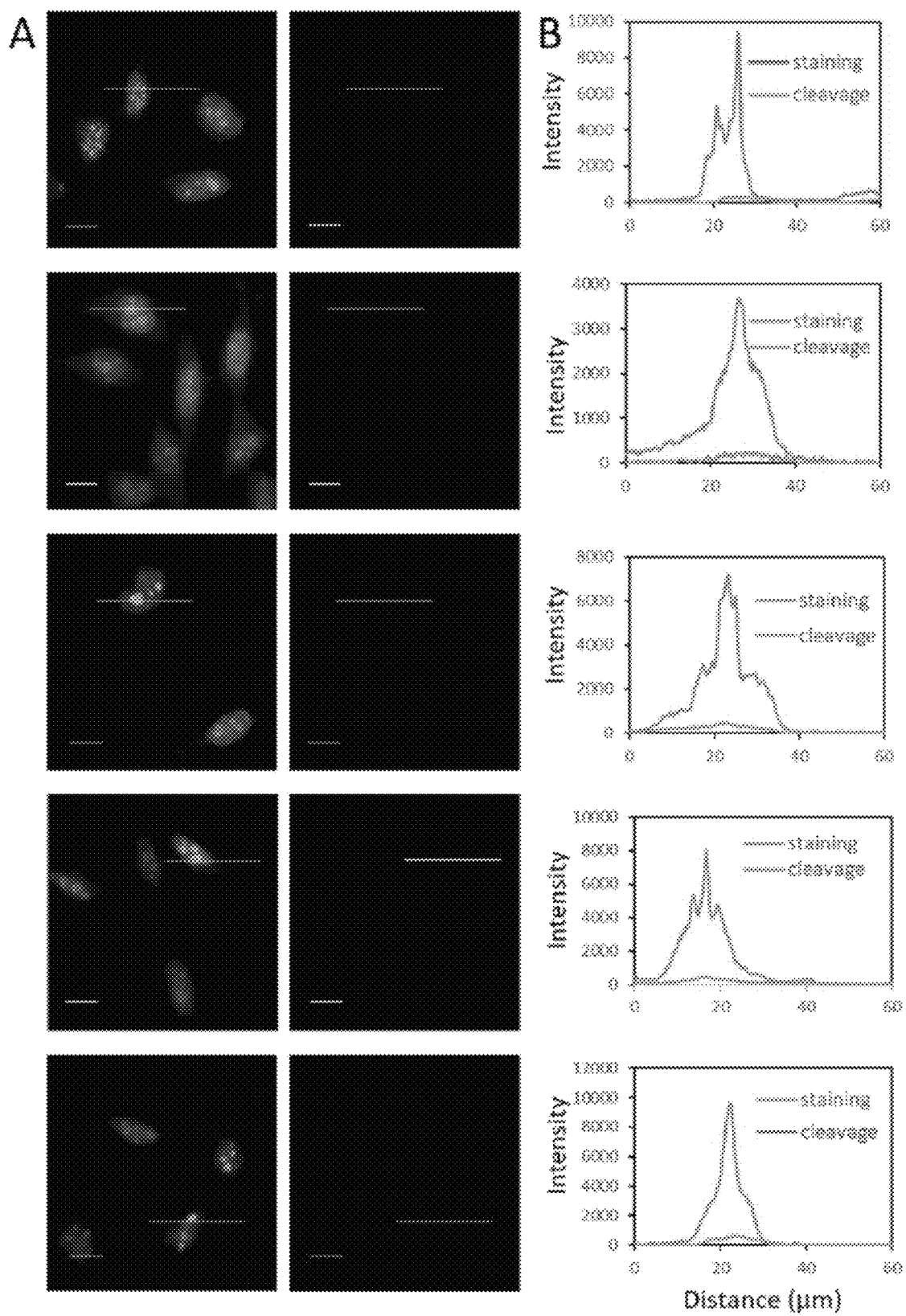
FIGS. 13A-13B. (A) Fluorescent images of protein Ki67 stained with 1 to 5 amplification cycles in Hela cells (left column) and those after cleavage (right column). The exposure time in amplification cycles 1 to 5 is 1 s, 500 ms, 250 ms, 125 ms, 62 ms, respectively. (B) Fluorescence intensity profiles corresponding to the indicated line positions in amplification cycles 1 to 5. Scale bars, 20 µm.
Figures 14A, 14B:
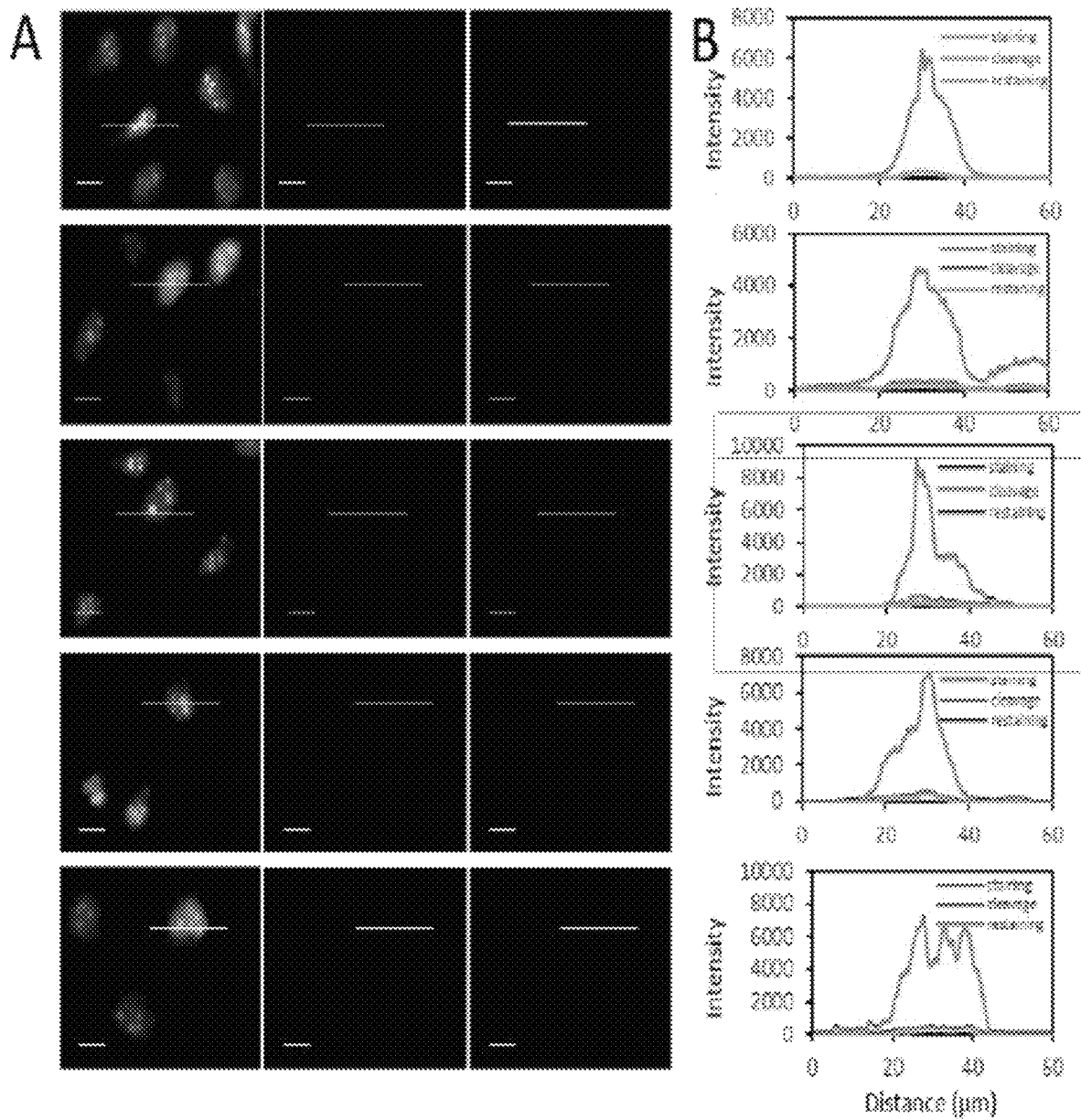
FIGS. 14A-14B. (A) Fluorescent images of protein Ki67 stained with 1 to 5 amplification cycles in HeLa cells (left column) and after cleavage (middle column) and restained with CFS (right column). The exposure time in amplification cycles 1 to 5 is 1 s, 500 ms, 250 ms, 125 ms, 62 ms, respectively. (B) Fluorescence intensity profiles corresponding to the indicated line positions in amplification cycles 1 to 5. Scale bars, 20 µm.
Figures 15A, 15B:
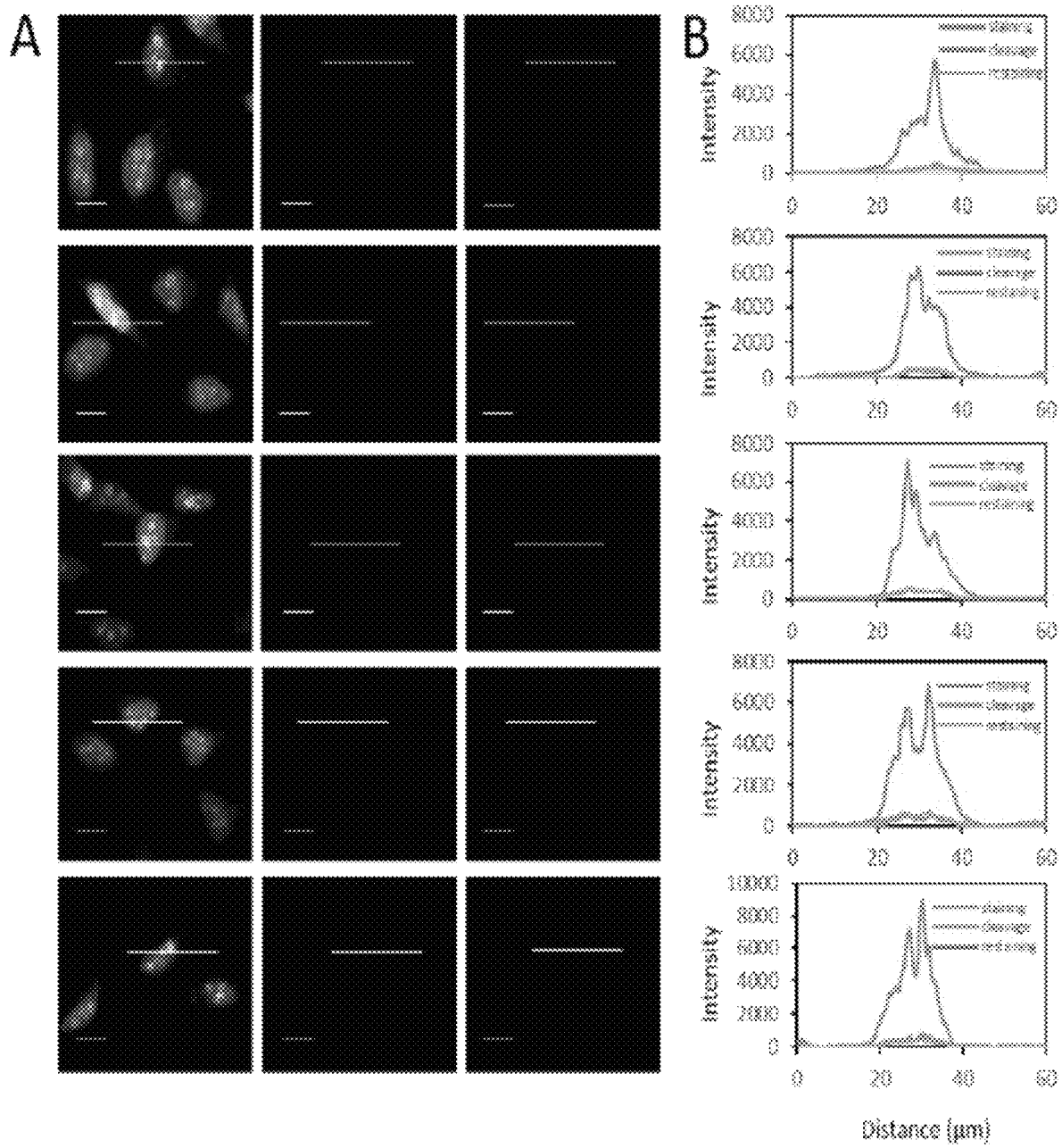
FIGS. 15A-15B. (A) Fluorescent images of protein Ki67 stained with 1 to 5 amplification cycles in HeLa cells (left column) and those after cleavage (middle column). Following streptavidin blocking, the cells were restained with cleavable biotin labeled antibodies and CFS (right column). The exposure time in amplification cycles 1 to 5 is 1 s, 500 ms, 250 ms, 125 ms, 62 ms, respectively. B) Fluorescence intensity profiles corresponding to the indicated line positions in amplification cycles 1 to 5. Scale bars, 20 µm.

The existing reiterative protein profiling methods requires one to know the relative protein expression levels in advance. With that prior knowledge, proteins are quantified in the order of increasing expression levels, to minimize the interference from the leftover signals generated in the previous cycles. However, due to the limited amount of the biological and clinical samples, to obtain that prior knowledge of protein expression levels is sometimes not possible. In addition, the relative protein expression levels in different cell types in the same specimen can be different, which makes it difficult to develop a desired protein analysis order for all the cell types. Moreover, the process to generate such prior knowledge can be time-consuming and expensive. Our CSF method addresses all of these issues by eliminating the requirement of knowing protein expression levels in advance. In this approach, the protein staining signal in each analysis cycle can be amplified with a certain number of amplification cycles until the satisfied staining intensities are achieved. In this way, following the analysis of high expression proteins in the previous cycles, the low expression proteins can be accurately quantified by more amplification cycles. To demonstrate the feasibility of this concept, protein H4K20me, Ki67 and c-erbB-2 was profiled in the same set of HeLa cells in the order of decreasing expression levels (FIGS. 8A-8C). As a result of efficient fluorophore and biotin cleavage and also efficient streptavidin blocking, protein Ki67 was successfully detected following the analysis of high expression H4K20me. However, due to the extremely low expression level of c-erbB-2 and the accumulated leftover signals produced in the previous two cycles, it was difficult to detect protein c-erbB-2 without signal amplification (FIG. 11). After one cycle of signal amplification, the staining signal of c-erbB-2 was significantly enhanced (FIGS. 8A and 8D). With the improved signal-to-background ratio, the low expression c-erbB-2 was unambiguously detected following the analysis of two high expression proteins. Additional fluorescent images of protein Ki67 stained with 1 to 5 amplification cycles in HeLa cells before and after cleavage and, in some cases, with re-staining are presented in FIGS. 12A-12B, FIGS. 13A-13B, FIGS. 14A-14B, and FIGS. 15A-15B. Together, the results presented herein indicate that the CFS method does not require the prior knowledge of protein expression levels and enables the accurate protein analysis regardless of the protein analysis orders.

Archived tissues are important biological samples to study normal physiology and disease pathogenesis. Formalin fixed, paraffin embedded (FFPE) tissue is the most common form of archived tissues in clinics and pathology labs. FFPE tissues often bear high autofluorescence and partially degraded proteins, which makes them difficult to be profiled by the fluorescence imaging methods with low detection sensitivities. To demonstrate the feasibility of applying the CFS approach to analyze FFPE tissues, a FFPE human brain tissue was stained for H3K4me3 (FIGS. 9A-9F). With 2 rounds of signal amplification, the signal-to-background ratio was significantly improved. After cleavage, the fluorescence signal was efficiently removed. Another round of signal amplification cycle after cleavage and streptavidin blocking did not further increase the staining intensities. These results confirm that the fluorophores and the free biotins can be efficiently removed by TCEP and streptavidin can be efficiently blocked by biotin. These results also suggest that the CFS approach can be successfully applied to quantify proteins, including partially degraded proteins, of FFPE tissues.

Discussion

In summary, cleavable fluorescent streptavidin was designed, synthesized, and applied for multiplexed in situ protein profiling. Compared with the existing multiplexed protein imaging technologies, our approach has enhanced the detection sensitivity by at least one order of magnitude. With the dramatically improved sensitivity, this approach enables the quantitative analysis of low expression proteins, especially in the highly autofluorescent FFPE tissue samples.

The multiplexing capacity of this approach depends on two factors: the number of reiterative analysis cycles and the number of proteins quantified in each cycle. The inventors have shown previously that the protein antigenicity is preserved after the incubation with TCEP for at least 24 hours, which suggests that more than 40 cycles can be carried out on the same specimen. In each cycle, varied protein targets can be first recognized by primary antibodies labeled with distinct cleavable haptens, such as biotin, fluorescein, TAMRA, and digoxigenin (DIG). Subsequently, streptavidin, anti-fluorescein, anti-TAMRA, and anti-DIG antibodies labeled with different fluorophores can be applied to stain the protein targets and amplify the signals. In this way, at least four proteins can be quantified simultaneously in each cycle. Thus, we anticipate this method has the potential to analyze over 100 protein targets in the same specimen.

In addition to protein profiling, this cleavable layer-by-layer signal amplification approach developed here can also be applied for highly sensitive in situ DNA, RNA, and metabolic analysis. By combining these applications, the integrated in situ genomics, proteomics and metabolomics analysis can be achieved in the same specimen at the optical resolution. This highly sensitive and multiplexed molecular imaging platform will have wide applications in systems biology and biomedical research.

The present invention has been described in terms of one or more preferred embodiments, and it should be appreciated that many equivalents, alternatives, variations, and modifications, aside from those expressly stated, are possible and within the scope of the invention.

We claim:

1. A method of multiplexed in situ analysis of biomolecules in a sample, the method comprising the following steps:
   (a) performing a first contacting step comprising contacting a sample comprising a plurality of biomolecules with a first hapten-conjugated targeting agent, the first hapten-conjugated targeting agent comprising a first targeting agent conjugated to the hapten via a cleavable linker, wherein the first targeting agent is configured to specifically bind or hybridize to a first target biomolecule in the sample, and wherein the first contacting step occurs under conditions that promote binding or hybridization of the first targeting agent to the first target biomolecule in the sample;
   (b) performing a second contacting step comprising contacting the sample of step (a) with a hapten-binding composition comprising a hapten-binding agent linked to a detectable label via a cleavable linker, wherein the second contacting step occurs under conditions that promote conjugation of the hapten-binding composition to the hapten of the first hapten-conjugated targeting agent;
(c) imaging the sample after step (b), whereby a detectable signal generated from an interaction of hapten-conjugated targeting agent with the hapten-binding composition is detected;
(d) cleaving the cleavable linkers to remove the detectable label from the hapten-binding composition and unbound hapten from the first hapten-conjugated targeting agent;
(e) blocking the remaining hapten-binding agent; and
(f) repeating the first contacting step, second contacting step, and imaging step with a second hapten-conjugated targeting agent, wherein the first hapten-conjugated targeting agent and the second hapten-conjugated targeting agent are configured to specifically bind or hybridize to a different target biomolecule, whereby multiple target biomolecules are detected in situ in the same sample.

2. The method of claim 1, wherein the steps are performed one or more additional times, using a unique plurality of hapten-conjugated targeting agents, wherein each unique hapten-conjugated targeting agent is configured to specifically bind or hybridize to a unique target biomolecule for each subsequent cycle.

3. The method of claim 1, wherein the target biomolecule is selected from the group consisting of proteins, RNA, DNA, peptide nucleic acids (PNAs), chemically modified oligonucleotides, locked nucleic acids, and combinations thereof.

4. The method of claim 1, wherein the hapten-conjugated targeting agent is selected from the group consisting of biotin-conjugated antibodies, biotin-conjugated synthetic oligonucleotide probes, and a combination thereof.

5. The method of claim 1, wherein the detectable label in the hapten-binding composition comprises a fluorophore.

6. The method of claim 5, wherein the cleavable linker in the hapten-binding composition is chemically cleavable, enzymatically cleavable, nucleophilically cleavable, electrophilically cleavable, photocleavable, metal cleavable, cleavable under reductive conditions, cleavable under oxidative conditions, cleavable using an acidic reagent, or cleavable using a basic reagent.

7. The method of claim 5, wherein the fluorophore is selected from the group consisting of Cy5, TAMRA, ALEXA FLUOR™ 594, ATTO 647N, ATTO 700, ALEXA FLUOR™ 350, ALEXA FLUOR™ 532, ALEXA FLUOR™ 546, ALEXA FLUOR™ 568, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, DYLIGHT™ 405, DYLIGHT™ 488, DYLIGHT™ 549, DYLIGHT™ 594, DYLIGHT™ 633, DYLIGHT™ 649, DYLIGHT™ 680, DYLIGHT™ 750, DYLIGHT™ 800, Texas Red, Cy2, Cy3.5, Cy5.5, and Cy7.

8. The method of claim 1, wherein the hapten-binding composition is streptavidin-N3-Cy5.

9. The method of claim 1, wherein removing the detectable label comprises chemically cleaving the detectable moiety from the hapten-binding composition.

10. The method of claim 1, further comprising washing to remove unhybridized targeting agents and non-specifically hybridized targeting agents following each second contacting step.

11. The method of claim 1, further comprising contacting the sample with a second orthogonal labeled antibody for signal amplification after step (b) or after step (c).

12. The method of claim 1, wherein the first targeting agent, the second targeting agent or both targeting agents comprises biotin-conjugated synthetic DNA oligonucleotide probes.

13. The method of claim 1, wherein the first targeting agent, the second targeting agent or both comprises hapten-conjugated polyclonal antibodies, hapten-conjugated monoclonal antibodies, or hapten-conjugated antigen-binding fragments thereof, wherein the hapten is selected from those listed in Table 1.

14. The method of claim 1, wherein the hapten is biotin and the hapten-binding agent is streptavidin.

15. The method of claim 1, wherein the sample is selected from a cell, a tissue, a paraffin embedded tissue section, a fresh tissue section, a frozen tissue section, a fixed tissue, fixed cells, or frozen cells.

16. A kit for detecting target biomolecules in a sample, the kit comprising a cleavable detectably-labeled hapten-binding agent, reagents for cleaving the cleavable detectably-labeled hapten-binding agent and a written insert component comprising instructions for performing multiplexed in situ analysis of target biomolecules according to the method of claim 1.

17. The kit of claim 16, wherein the cleavable detectably-labeled hapten-binding agent is streptavidin-N3-Cy5.

18. The kit of claim 16, wherein the kit further comprises a plurality of hapten-conjugated targeting agents configured to bind or hybridize to a target biomolecule, wherein the hapten is selected from those listed in Table 1.

19. The kit of claim 18, wherein the hapten-conjugated targeting agents comprises hapten-conjugated polyclonal or monoclonal antibodies, or antigen-binding fragments thereof or hapten-conjugated synthetic oligonucleotide probes.

20. The kit of claim 16, wherein the kit further comprises tris(2-carboxyethyl)phosphine (TCEP) and wherein the written instruction component further comprises instructions for removing the detectable label from the detectably-labeled hapten-binding agent using the TCEP.

* * * * *